United States Patent
Scadden et al.

(10) Patent No.: US 9,750,767 B2
(45) Date of Patent: Sep. 5, 2017

(54) IL-18 INHIBITION FOR PROMOTION OF EARLY HEMATOPOIETIC PROGENITOR EXPANSION

(71) Applicants: THE GENERAL HOSPITAL CORPORATION, Boston, MA (US); PRESIDENT AND FELLOWS OF HARVARD COLLEGE, Cambridge, MA (US)

(72) Inventors: David T. Scadden, Weston, MA (US); Lev Silberstein, Brookline, MA (US); Peter Kharchenko, Brookline, MA (US)

(73) Assignees: THE GENERAL HOSPITAL CORPORATION, Boston, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 21 days.

(21) Appl. No.: 14/760,076

(22) PCT Filed: Jan. 14, 2014

(86) PCT No.: PCT/US2014/011445
§ 371 (c)(1),
(2) Date: Jul. 9, 2015

(87) PCT Pub. No.: WO2014/110560
PCT Pub. Date: Jul. 17, 2014

(65) Prior Publication Data
US 2016/0030481 A1    Feb. 4, 2016

Related U.S. Application Data

(60) Provisional application No. 61/752,179, filed on Jan. 14, 2013.

(51) Int. Cl.
*A61K 35/28*    (2015.01)
*A61K 38/17*    (2006.01)
*A61K 38/20*    (2006.01)
*A61K 35/12*    (2015.01)

(52) U.S. Cl.
CPC .......... *A61K 35/28* (2013.01); *A61K 38/1709* (2013.01); *A61K 38/20* (2013.01); *A61K 2035/124* (2013.01)

(58) Field of Classification Search
CPC .... A61K 35/28; A61K 38/1709; A61K 38/20; A61K 2035/124
See application file for complete search history.

(56) References Cited

U.S. PATENT DOCUMENTS 8,858,944 B2    10/2014    Kino et al.

FOREIGN PATENT DOCUMENTS

WO    2006/019357 A1    2/2006

OTHER PUBLICATIONS

Min et al., Blood. Nov. 15, 2004;104(10):3393-3399.*
Bourdeau et al., "Inhibition of T cell protein tyrosine phosphatase enhances interleukin-18-dependent hematopoietic stem cell expansion", Stem Cells. 31(2):293-304 (2013).
Pelloso et al., "Immunological consequences of interleukin 12 administration after autologous stem cell transplantation", Clin Cancer Res. 10(6):1935-42 (2004).
Shaiegan et al., "Effect of IL-18 and sIL2R on aGVHD occurrence after hematopoietic stem cell transplantation in some Iranian patients", Transpl Immunol. 15(3):223-7 (2006).
Gerber et al., "The role of VEGF in normal and neoplastic hematopoiesis", J. Mol. Med. 81(1):20-31 (2003).
Pridans et al., "Identification of Pax5 target genes in early B cell differentiation.", The Journal of Immunology 180(3):1719-1728 (2008).
Yang et al., "Identification of Lin-Sca1+ kit+ CD34+ Flt3-short-term hematopoietic stem cells capable of rapidly reconstituting and rescuing myeloablated transplant recipients.", Blood 105(7):2717-2723 (2005).

* cited by examiner

*Primary Examiner* — Daniel C Gamett
(74) *Attorney, Agent, or Firm* — Nixon Peabody LLP; David S. Resnick; Shayne Y. Huff

(57) ABSTRACT

Disclosed herein are methods for enhancing hematopoietic reconstitution of a subject. One method involves administering a therapeutically effective amount of an inhibitor of IL-18 to a recipient subject and also administering hematopoietic stem/progenitor cells to the subject. Another method involves administering an inhibitor of IL-18 to a donor prior to harvest of hematopoietic stem/progenitor cells. Pharmaceutical compositions relating to the methods are also described.

20 Claims, 15 Drawing Sheets

IL-18 INHIBITION FOR PROMOTION OF EARLY HEMATOPOIETIC PROGENITOR EXPANSION

CROSS-REFERENCE TO RELATED APPLICATIONS

This application is a 371 National Phase Entry of International Patent Application No. PCT/US2014/011445 filed on Jan. 14, 2014 which claims the benefit under 35 U.S.C. §119(e) of U.S. Provisional Application Ser. No. 61/752,179, filed Jan. 14, 2013, the contents of which are incorporated herein by reference in their entirety.

GOVERNMENTAL SUPPORT

This invention was made with Government support under grants K25AG037596, R01DK050234-15A1, and R01HL097794-03, awarded by the National Institute of Health. The Government has certain rights in the invention.

SEQUENCE LISTING

The instant application contains a Sequence Listing which has been submitted electronically in ASCII format and is hereby incorporated by reference in its entirety. Said ASCII copy, created on Oct. 20, 2015, is named 030258-076612-US_SL.txt and is 2,928 bytes in size.

FIELD OF THE INVENTION

The present invention relates to the field of hematopoietic cell transplantation.

BACKGROUND OF THE INVENTION

Post-transplant bone marrow aplasia is a major cause of morbidity and mortality after bone marrow transplant (BMT). Enhancing proliferation of short-term repopulating progenitors is an attractive strategy to accelerate post-transplant hematopoietic recovery, since the early reconstituting ability of these cells appears to be superior to that of long-term HCSs (LT-HSC). However, previously characterized extrinsic molecular pathways governing kinetics of short-term repopulating cells are also known to control LT-HSCs, raising a concern that manipulating those pathways in the transplant setting may lead to LT-HSC exhaustion.

Hematopoietic system is hierarchically organized and consists of 3 main compartments—slow dividing long-term stem cells, very rapidly dividing progenitors and non-dividing mature cells (the "effector" compartment)—all of which have distinct cell-surface marker profile. Stem cells support hematopoiesis throughout life-time, while progenitors have a capacity for massive short-term expansion in response to environmental stimuli such as infection or stress in order to generate a large number of mature blood cells. Long-term stem cells are absolutely required and sufficient for hematopoietic reconstitution following myeloablation. However, they are not as efficient at giving rise to mature cells as compared to more differentiating progenitors (Yang et al. Blood. 2005; 105:2717-2723). Cord blood, mobilized peripheral blood stem cells and bone marrow are currently used as a source of long-term hematopoietic stem cells in clinical bone marrow transplantation. All these products contain, together with stem cells, a variable proportion of hematopoietic progenitors.

SUMMARY OF THE INVENTION

One aspect of the invention relates to a method for enhancing hematopoietic reconstitution of a subject in need thereof comprising administering to the subject hematopoietic stem/progenitor cells (HSPC), and administering to the subject a therapeutically effective amount of an inhibitor of interleukin 18 (IL-18) to thereby inhibit IL-18 interaction with IL-18R molecules present on the HSPC administered in step a).

In one embodiment, the inhibitor of IL-18 is administered to thereby contact the administered HSPC.

In one embodiment of the methods described herein, administering is by a route selected from the group consisting of enteral and parenteral.

In one embodiment of the methods described herein, administering of the inhibitor is performed immediately after administering of the HSPC.

In one embodiment of the methods described herein, administering of the inhibitor is performed prior to and immediately after administering of the HSPC.

In one embodiment of the methods described herein, the inhibitor of IL-18 is administered to the subject over a period of time from about 1 day to 100 days directly after administration of the HSPCs.

In one embodiment of the methods described herein, the period is from about 1 day to about 21 days directly after administration of the HSPCs.

In one embodiment of the methods described herein, the period is from about 1 day to about 5 days directly after administration of the HSPCs.

In one embodiment of the methods described herein, the period is about 5 days directly after administration of the HSPCs.

In one embodiment of the methods described herein, the HSPCs are allogenic.

In one embodiment of the methods described herein, the HSPCs are autologous.

In one embodiment of the methods described herein, the HSPC are obtained from a donor subject treated with an inhibitor of IL-18 prior to harvest of the HSPCs to thereby expand early hematopoietic progenitor cells in the HSPCs.

Another aspect of the invention relates to a method for enhanced hematopoietic reconstitution in a subject in need thereof comprising administering to the subject hematopoietic stem/progenitor cells (HSPC) obtained from a donor subject, wherein the donor subject was treated with an inhibitor of interleukin 18 (IL-18) to thereby expand early hematopoietic progenitor cells prior to harvest of the HSPCs from the donor.

In one embodiment of the methods described herein, the donor subject is treated with the inhibitor of IL-18 for a period of from about 1 day to about 10 days directly prior to harvest of the HSPCs.

In one embodiment of the methods described herein, the period is from about 1 day to about 5 days directly prior to harvest of the HSPCs.

In one embodiment of the methods described herein, the period is about 5 days directly prior to harvest of the HSPCs.

In one embodiment of the methods described herein, the treatment of the donor subject is by administration of the inhibitor of IL-18 to the donor subject by a method selected from the group consisting of enteral and parenteral.

In one embodiment of the methods described herein, the HSPCs are obtained from bone marrow, blood, placenta, or umbilical cord of the donor.

In one embodiment of the methods described herein, the inhibitor of IL-18 is selected from the group consisting of IL-18 binding protein, an antibody against IL-18, an antibody against an IL-18 receptor subunits, an inhibitor of the IL-18 signaling pathway, an antagonist of IL-18 which competes with IL-18 and blocks the IL-18 receptor, an inhibitor of caspase-1 (ICE), an IL-18 isoform, an IL-18 mutein, an IL-18 fused protein, an IL-18 functional derivative, an IL-18 active fraction, and an IL-18 circularly permutated derivative thereof inhibiting the biological activity of IL-18.

Definitions

An "effective amount" as the term is used herein, is used to refer to an amount that is sufficient to produce at least a reproducibly detectable amount of the desired results. In the context of the invention, effective amounts are amounts that inhibit IL-18 signaling (e.g., by inhibiting the IL-18: IL-18R interaction) of a target multipotent progenitor hematopoietic cell. One example of an effective amount is an amount that results in substantial inhibition of IL-18 receptor signaling in the progenitor cells. Substantial inhibition may comprise inhibition of greater than about 40%, 50%, 60%, 70%, 80%, or 90% of signaling. Such inhibition can be measured directly or indirectly. Direct measurement involves identification of receptor binding, or other direct measurements of IL-18R activity such as downstream signaling events. Indirect measurement involves quantitation of overall cellular activity, such as cellular proliferation and differentiation. An effective amount will vary with the specific conditions and circumstances. Such an amount can be determined by the skilled practitioner for a given situation. The effective amounts can be provided all at once in a single administration or in fractional amounts that provide the effective amount in several administrations.

The term "therapeutically effective amount" refers to an amount that is sufficient to effect a therapeutically significant reduction in one or more symptoms of the condition when administered to a typical subject who has the condition. A therapeutically significant reduction in a symptom or complication resulting from the transplant, or increase in re-populating neutrophils and lymphocytes in an HSPC transplant recipient is, e.g. about 10%, about 20%, about 30%, about 40%, about 50%, about 60%, about 70%, about 80%, about 90%, about 100%, or more (e.g., 1.5 fold, 2 fold, 3 fold, 4 fold, 5 fold, 10 fold, 25 fold, 50 fold, 100 fold, etc.) as compared to a control or non-treated subject. The term "therapeutically effective amount" refers to the amount of an agent determined to produce any therapeutic response in a subject. For example, a therapeutically effective amount of an inhibitor of IL-18 may increase the number of neutrophils and lymphocytes in an HSPC transplant recipient over time as compared to a similar transplant recipient who has not received the inhibitor. This is expected to occur during the early stages of repopulation, the critical time period being up to 100 days post-transplant (e.g., within days 1, 2, 3, 4, 5, 5-10, or within 1, 2, 3, or 4 weeks, 1, 2, or 3 months). This will reduce or eliminate the development of complications following transplant and reduce mortality from complications. Complications following transplant include, without limitation, graft-vs-host disease (GvHD), bacterial infections, fungal infections, viral infections, gastrointestinal and hepatic complications, neurologic complications, and pulmonary complications.

Treatments that are therapeutically effective within the meaning of the term as used herein, include treatments that reduce or eliminate complications experienced by the transplant recipients within the critical post-transplant time frame discussed herein. Such therapeutically effective amounts are readily ascertained by one of ordinary skill in the art. Thus, to "treat" means to deliver such an amount.

The precise determination of what would be considered a therapeutically effective amount may be based on factors individual to each subject, including their size, age, injury, and/or disease or injury being treated, and amount of time since the injury occurred or the disease began. One skilled in the art will be able to determine the therapeutically effective amount for a given subject based on these considerations which are routine in the art.

The term "treat" or "treatment" refers to therapeutic treatment wherein the object is to eliminate or lessen symptoms. Beneficial or desired clinical results include, but are not limited to, elimination of symptoms, alleviation of symptoms, diminishment of extent of condition, stabilized (i.e., not worsening) state of condition, delay or slowing of progression of the condition.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with unwanted neuronal activity. In addition, the methods and compositions described herein can be used to treat domesticated animals and/or pets.

The terms "patient", "subject" and "individual" are used interchangeably herein, and refer to an animal, particularly a human, to whom treatment is provided. This includes human and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows. In one embodiment, the subject is human. In another embodiment, the subject is an experimental animal or animal substitute as a disease model. "Mammal" refers to any animal classified as a mammal, including humans, non-human primates, domestic and farm animals, and zoo, sports, or pet animals, such as dogs, cats, cattle, horses, sheep, pigs, goats, rabbits, etc. Patient or subject includes any subset of the foregoing, e.g., all of the above, but excluding one or more groups or species such as humans, primates or rodents. A subject can be male or female. A subject can be a fully developed subject (e.g., an adult) or a subject undergoing the developmental process (e.g., a child, infant or fetus).

DETAILED DESCRIPTION OF THE INVENTION

Figure 1:
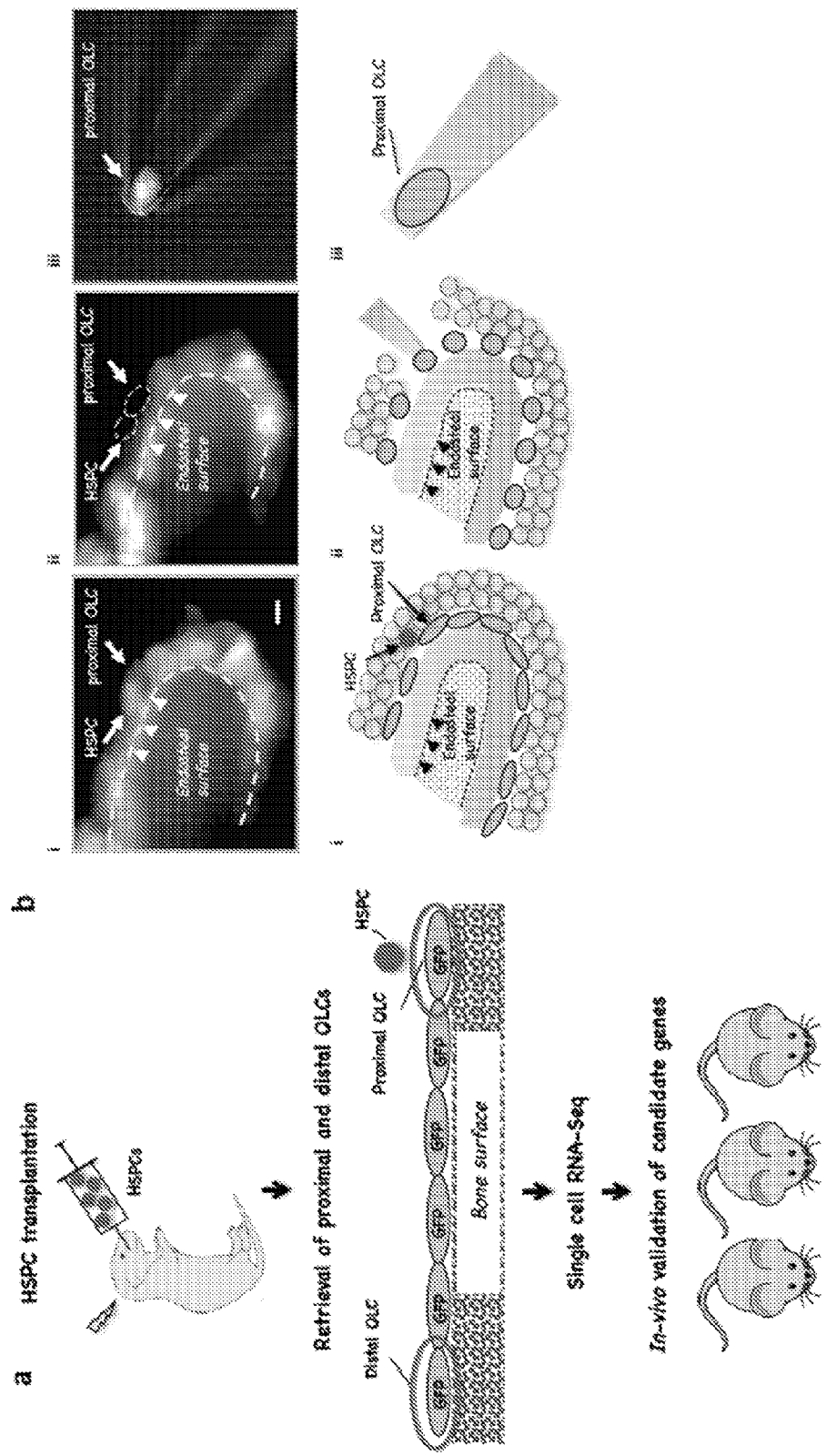
FIG. 1A-FIG. 1B outlines the proximity-based single cell approach to the study of HSPC niche. A) DiI-labeled adult bone marrow LKS CD34$^-$Flk2$^-$ HSPCs were intravenously injected into irradiated col2.3GFP pups (P2). Forty-eight hours later, fresh sections of the femori were obtained, individual HSPC-proximal and HSPC-distal OLCs were identified and harvested for single cell RNA-Seq analysis. Selected differentially expressed genes were validated in vivo. B) Micropipette aspiration was used to retrieve individual OLCs directly from a thick (100µ) fresh section of neonatal mouse femur. Shown are overlaid single color (GFP and DiI) images before and after retrieval of HSPC-proximal OLC (top panel: microphotographs, bottom panel: corresponding schematic diagram). Scale bar: 10 µm. (i) The HSCP-proximal GFP$^+$ OLC (green) was identified based on proximity to the DiI-labeled HSPC (red). (ii) Following in-situ enzymatic dissociation, the HSPC is dislodged from its original location, other hematopoietic cells become loose and OLC partially detaches from the endosteal surface. (iii) Target OLC is aspirated into a micropipette.

Interleukin-18, a pro-inflammatory cytokine, is a newly identified non-cell autonomous regulator of quiescence, which selectively regulates short-term progenitors. IL18 receptor is not expressed in long-term HSCs, but is present in ST-HSCs and multi-potent progenitors; in IL18KO mice, a greater proportion of these cells were in S/G2/M phase of cell cycle, while the kinetics of LT-HSCs were unchanged. Notably, IL18KO recipients of WT bone marrow displayed faster peripheral blood lymphoid recovery during weeks 4-12 (both in primary and secondary transplants), while no changes in LT-HSC frequency and absolute number at 16 weeks post-transplant were detected.

Aspects of the invention relate to the findings reported herein that interleukin 18 (IL-18) interaction with the IL-18 receptor (IL-18R) induces quiescence of multipotent hematopoietic cells. Inhibition of IL-18 receptor signaling (e.g., by disruption of the IL-18: IL-18R interaction) on multipotent progenitor cells leads to the expansion of early hematopoietic progenitor cells. Aspects of the invention also relate to the finding that disruption of the IL-18: IL-18R interaction does not affect stem cells, and as such, inhibition of IL-18 receptor signaling does not cause expansion of long term hematopoietic stem cells and therefore does not lead to stem cell exhaustion. These findings can be applied to existing methods for hematopoietic reconstitution (such as bone marrow transplant) to enhance the proliferation of short term repopulating progenitor cells and/or development into neutrophils and lymphocytes in a subject to accelerate post-transplant recovery. Such accelerated recovery will reduce the risk of infection and hemorrhagic complications, and in turn reduce post-transplant morbidity and mortality.

One aspect of the invention relates to a method for hematopoietic reconstitution in a subject. The method involves administering to the subject hematopoietic stem/progenitor cells (HSPC) and administering to the subject a therapeutically effective amount of an inhibitor of IL-18 receptor signaling (e.g. an inhibitor of IL-18). The inhibitor is administered by a route and in a sufficient amount to thereby contact the HSPCs in the subject (e.g., those that express IL-18R at significant levels) and thereby promote enhanced proliferation and expansion of the early hematopoietic cells therein. The hematopoietic reconstitution in the subject which would otherwise occur in the absence of the inhibitor is thereby enhanced by the activity of the inhibitor in that the short term reconstitution occurs faster and/or more completely (e.g., with enhanced differentiation into a broader range of cell types) than otherwise would have occurred in the absence of the inhibitor.

A recipient subject in the methods described herein can be anyone in need of hematopoietic reconstitution or anyone with reduced number of white blood cells in peripheral blood. Such subjects include, without limitation, subjects with hematopoietic cancer such as leukemia and lymphoma, subjects with myelosuppression or myeloablation, such as those who have undergone cytoreductive therapy (e.g., chemotherapy or radiation therapy). The recipient subject may suffer from diseases and disorders including, without limitation, leukopenia of various origins including, congenital leukopenia, childhood or adult cyclic neutropenia, post-infective neutropenia, and myelodysplastic syndrome and aplastic anemia (congenital and acquired). Subjects suitable as recipients include those in which their entire hematopoietic system is ablated, and also those with reduced intensity conditioning. Reduced intensity conditioning does not result in complete myeloablation and is used in patients that are older, in patients who are in complete remission, and in patients with acquired aplastic anemia.

In one embodiment, the donor has been identified or selected as a candidate for donation of HSPCs prior to administration of the inhibitor of IL-18. In one embodiment, the donor undergoes additional conditioning prior to administration of the HSPCs.

Timing of Inhibitor Administration

Administration of the inhibitor to the recipient subject may be prior to, concurrent with, or after administration of the HSPC. It may be advantageous for administration to be ongoing over a period of time, beginning prior to, concurrent with or after administration of the HSPC. Such ongoing administration could be by way of multiple administration time points. In one embodiment, the inhibitor is administered to the subject for a period of from about 1 day to about 5 days (e.g., about 5, 4, 3, 2 or 1 days) beginning on the day of administration of the HSPC. In one embodiment, the inhibitor is administered to the subject for a period of from about 5 days to about 10 days (e.g., about 10, 9, 8, 7, or 6 days) beginning on the day of administration of the HSPC. In one embodiment, the inhibitor is administered to the subject for a period of from about 10 days to about 20 days (e.g., about 20, 19, 18, 17, 16, 15, 14, 13, 12, or 11 days) beginning on the day of administration of the HSPC. In one embodiment, the inhibitor is administered to the subject for a period of from about 20 days to about 30 days (e.g., about 30, 29, 28, 27, 26, 25, 24, 23, 22, or 21 days) beginning on the day of administration of the HSPC. Benefit may also be obtained from administration on a regular basis up to about day 100 of the HSPC administration.

Administration of the inhibitor at the time of administration of the HSPC encompasses administration concurrently with the HSPCs, directly prior to (e.g., within an hour prior), and also directly following administration of the HSPC (e.g., within about 1-24 hours). Administration concurrently with the HSPCs may also include combining the HSPCs with the inhibitor and administering the combination to the subject.

Administration of the inhibitor to the subject prior to administration of the HSPC is expected to have beneficial effect. Administration for a period of from about 1 day up to about 5 days (e.g., about 5, 4, 3, 2 or 1 day) prior to administration of the HSPCs is envisioned. In one embodiment, administration of the inhibitor prior to receipt is combined with administration at the time of receipt and/or ongoing administration for a period of time as described herein.

Source of HSPCs

HSPCs are determined suitable for hematopoietic reconstitution by the skilled practitioner, including identification of a suitable donor, appropriate collection and manipulation, prior to administration to the subject.

The HSPCs can be autologous (where the donor and recipient are the same person) and allogeneic (where the donor and recipient are different individuals). In autologous transplant, HSPCs are removed from the subject before they experience the hematopoietic damaging event (e.g., high-dose chemotherapy or radiation treatment). The cells are stored in a freezer (cryopreservation). After the damaging event, the cells are put back in the subject's body to make (regenerate) normal blood cells. This is referred to as a rescue transplant. In allogeneic transplant, HSPCs are removed from another person, referred to as a donor. Umbilical cord blood transplant is a type of allogeneic or autologous transplant depending on the source of the umbilical cord. Stem cells are removed from a newborn baby's umbilical cord right after birth. The stem cells are frozen and stored until they are needed for a transplant. Another source of donor cells is placenta.

Another source of donor cells is alternative sources requiring genetic manipulation such as HSCs obtained through genetic re-programming of more mature cells or induced embryonic stem cells.

Donor HSPCs are typically collected in two ways, by bone marrow harvest or leukapheresis. Bone marrow harvest is minor surgery performed under general anesthesia, where the bone marrow is removed from the back of both hip bones. Leukapheresis is the peripheral harvest of HSPCS. The donor receives several (e.g., about 5 days) of treatments to move stem cells from the bone marrow into the blood. During leukapheresis, blood is removed from the donor through an IV line in a vein. HSPCs are separated in a machine and removed to be later given to the recipient. The red blood cells are returned to the donor.

The harvested cells are a mixture of stem cells, progenitors, and white blood cells of various degrees of maturity. The progenitor cells and/or stem cells can reconstitute all of the hematopoietic cells in a subject. These include, but are not limited to, lymphocytes, platelets, erythrocytes and myeloid cells, including, T cells, B cells (plasma cells), natural killer cells, dendritic cells, monocytes (macrophages), neutrophils, eosinophils, basophils (mast cells), megakaryocytes (platelets), and erythroblasts (erythrocytes). These cells are also capable, in addition to differentiation, of self-renewal, so as to proliferate the stem-progenitor population that is capable of differentiation.

Treatment of the Donor

Another aspect of the invention relates to treatment of a donor individual with an inhibitor of IL-18 prior to donation of the HSPC for use in hematopoietic reconstitution in a subject. Hematopoietic reconstitution is achieved in a subject by administering to the subject HSPC obtained from a donor subject that was previously treated with an inhibitor of IL-18 receptor signaling (e.g. an inhibitor of IL-18), described herein. The treatment is to thereby induce expansion of early hematopoietic progenitor cells in the donor prior to harvest. The induction occurs by similar mechanism as in the recipient subject. The donor is treated with the inhibitor to thereby contact the HSPCs of the donor with an effective amount of the inhibitor. The inhibitor is administered by a route and in sufficient amount to thereby affect the HSPCs in the donor (e.g., those that express IL-18R at significant levels) and thereby promote enhanced proliferation and expansion of those cells. In one embodiment, administered by a route and in sufficient amount to thereby contact the HSPCs in the donor. As a result of the treatment, the enhanced proliferation and expansion may occur either in the donor prior to harvest, in the recipient following transplant, ex vivo, or any combination thereof. The hematopoietic reconstitution of the recipient subject is enhanced by the activity of the inhibitor in that the short term reconstitution occurs faster and/or more completely (e.g., with a broader cell type populations) than otherwise would have occurred in the absence of administration of the inhibitor to the donor.

Administration to the donor can be by a variety of methods, examples of which are described herein (e.g., those for the recipient). In one embodiment, the donor is also the recipient of the transplant. In one embodiment, the donor is different from the recipient of the transplant. In one embodiment, the recipient is also administered a therapeutically effective amount of an inhibitor, by the methods discussed herein.

Timing of Administration to the Donor

Administration of the inhibitor to the donor subject is prior to harvest of the HSPC. Administration may be in a single dose, or by way of multiple separate administrations over a period of time, beginning at a defined time point prior to harvest. In one embodiment, the inhibitor is administered to the subject for a period of from about 1 day to about 5 days (e.g., about 5, 4, 3, 2 or 1 days) prior to harvest of the HSPC. In one embodiment, the inhibitor is administered to the subject for a period of from about 5 days to about 10 days (e.g., about 10, 9, 8, 7, or 6 days) prior to harvest of the HSPC. In one embodiment, the inhibitor is administered to the subject for a period of from about 10 days to about 20 days (e.g., about 20, 19, 18, 17, 16, 15, 14, 13, 12, or 11 days) prior to harvest of the HSPC. In one embodiment, the inhibitor is administered to the subject for a period of from about 20 days to about 30 days (e.g., about 30, 29, 28, 27, 26, 25, 24, 23, 22, or 21 days) prior to harvest of the HSPC.

Donor cells may be obtained from any suitable source from the donor, examples of which are described herein.

Ex Vivo Administration to the HSPC

The results presented herein also indicate that treatment of the HSPC after harvest but prior to administration (ex vivo) with the inhibitor of IL-18 will also enhance expansion of the early hematopoietic progenitor cells. Such expansion is beneficial to the recipient subject and will accelerate post-transplant recovery, as described herein.

Interleukin 18

The cytokine interleukin 18 (IL-18) was initially described as an interferon-γ (IFN-γ) inducing factor (Nakamura et al., Infect. Immun. 57, 590-595 1989). It is an early signal in the development of T-lymphocyte helper cell type 1 (TH1) responses. IL-18 acts together with IL-12, IL-2, antigens, mitogens, and possibly further factors, to induce the production of IFN-γ. IL-18 also enhances the production of GM-CSF and IL-2, potentiates anti-CD3 induced T cell proliferation, and increases Fas-mediated killing of natural killer cells. Mature IL-18 is produced from its precursor by the IL-18 converting enzyme (ICE, caspase-1).

The IL-18 receptor consists of at least two components, co-operating in ligand binding. High- and low-affinity binding sites for IL-18 were found in murine IL-12 stimulated T cells (Yoshimoto et al., 1998, J. Immunol. 161, 3400-3407), suggesting a multiple chain receptor complex. Two receptor subunits have been identified, both belonging to the IL-1 receptor family (Parnet et al., 1996, J. Biol. Chem. 271, 3967-3970; Kim et al., J. Immuno. 2001,166, pp. 148-154). The signal transduction of IL-18 involves activation of NF-kB (DiDonato et al., 1997, Nature 388, 16514-16517). The IL-18 receptor complex consists of two receptor chains: a ligand-binding chain termed the IL-18R α chain and a signal-transducing chain termed the IL-18R β chain.

Interleukin 18 Inhibitors

The term "inhibitor of IL-18" within the context of this invention refers to any molecule modulating IL-18 production and/or action in such a way that IL-18 production and/or activation or signaling through the IL-18 Receptor is attenuated, reduced, or partially, substantially or completely prevented or blocked. An inhibitor of production can be any molecule negatively affecting the synthesis, processing or maturation of IL-18. The inhibitors considered according to the invention can be, for example, suppressors of gene expression of the interleukin IL-18, antisense mRNAs reducing or preventing the transcription of the IL-18 mRNA or leading to degradation of the mRNA, proteins impairing correct folding, or partially or substantially preventing secretion of IL-18, proteases degrading IL-18, once it has been synthesized, inhibitors of proteases cleaving pro-IL-18 in order to generate mature IL-18, such as inhibitors of caspase-1, and the like.

Examples of inhibitors of IL-18 include, without limitation, an IL-18BP, or an isoform, a mutein, fused protein, functional derivative, active fraction or circularly permutated derivative thereof. These isoforms, muteins, fused proteins or functional derivatives retain the biological activity of IL-18BP, in particular the binding to IL-18, and preferably have essentially at least an activity similar to IL-18BP. Ideally, such proteins have an enhanced biological activity as compared to unmodified IL-18BP. Preferred active fractions have an activity which is better than the activity of IL-18BP, or which have further advantages, like a better stability or a lower toxicity or immunogenicity, or they are easier to produce in large quantities, or easier to purify. Functional derivatives of IL-18BP may be conjugated to polymers in order to improve the properties of the protein, such as the stability, half-life, bioavailability, tolerance by the human body, or immunogenicity. To achieve this goal, IL18-BP may be linked e.g. to Polyethlyenglycol (PEG). PEGylation may be carried out by known methods, described in WO 92/13095, for example.

Administration of a combination of two or more inhibitors such as those described herein is also envisioned.

An inhibitor of IL-18 action can be an IL-18 antagonist, for example. Antagonists can either bind to or sequester the IL-18 molecule itself with sufficient affinity and specificity to partially or substantially neutralize the IL-18 or IL-18 binding site(s) responsible for IL-18 binding to the IL-18 Receptor. An antagonist may also inhibit the IL-18 signaling pathway, which is activated within the cells upon IL-18/receptor binding.

Inhibitors of IL-18 action may also be soluble IL-18 receptors or molecules mimicking the receptors, or agents blocking the IL-18 receptors, or IL-18 antibodies, such as polyclonal or monoclonal antibodies, or any other agent or molecule preventing the binding of IL-18 to its targets, thus diminishing or preventing triggering of the intra- or extra-cellular reactions mediated by IL-18.

In one embodiment, the inhibitor of IL-18 is an inhibitor of caspase-1 (ICE), neutralizing antibodies directed against IL-18, neutralizing antibodies directed against any of the IL-18 receptor subunits, inhibitors of the IL-18 signaling pathway, antagonists of IL-18 which compete with IL-18 and block the IL-18 receptor, and IL-18 binding proteins, isoforms, muteins, fused proteins, functional derivatives, active fractions or circularly permutated derivatives thereof inhibiting the biological activity of IL-18.

In one embodiment, the inhibitor of IL-18 is IL-18 binding protein (IL-18BP). This is a soluble protein having a high affinity for IL-18. IL-18BP has been isolated from human urine, and the human and mouse cDNAs as well as the human gene were cloned (Novick et. al., 1999, Immunity 10, 127-136; WO 99/09063). IL-18BP is not the extracellular domain of one of the known IL18 receptors, but a secreted, naturally circulating protein. It belongs to a novel family of secreted proteins, further including several Poxvirus-encoded proteins (Novick et al., 1999). Urinary as well as recombinant IL-18BP specifically bind IL-18 with a high affinity and down modulates the biological affinity of IL-18. The IL-18BP gene was localised to the human chromosome 11q13, and no exon coding for a transmembrane domain was found in an 8.3 kb genomic sequence. Four splice variants or isoforms of IL-18BP generated by alternative mRNA splicing have been found in humans so far. They were designated IL-18BP a, b, c and d, all sharing the same N-terminus and differing in the C-terminus (Novick et al, 1999). These isoforms vary in their ability to bind IL-18. Of the four, hIL-18BP isoforms a and c are known to have the strongest neutralizing capacity for IL-18. Human IL-18BP isoform a cross-reacts with murine IL-18.

The term "IL-18 binding protein" is used herein synonymously "IL18BP" and refers to such IL-18 binding proteins as those defined in WO 99/09063 or in Novick et al., 1999, including splice variants and/or isoforms of IL-18 binding proteins, as defined in Kim et al., 2000, which bind to IL-18. In particular, human isoforms a and c of IL-18BP are useful in accordance with the presence invention. The proteins useful according to the present invention may be glycosylated or non-glycosylated, they may be derived from natural sources, such as urine, or they may preferably be produced recombinantly. Recombinant expression may be carried out in prokaryotic expression systems like *E. coli*, or in eukaryotic, and preferably in mammalian, expression systems.

As used herein the term "muteins" refers to analogs of an IL-18BP, or analogs of a viral IL-18BP, in which one or more of the amino acid residues of a natural IL-18BP or viral IL-18BP are replaced by different amino acid residues, or are deleted, or one or more amino acid residues are added to the natural sequence of an IL-18BP, or a viral IL-18BP, without changing considerably the activity of the resulting products as compared with the wild type IL-18BP or viral IL-18BP. These muteins are prepared by known synthesis and/or by site-directed mutagenesis techniques, or any other known technique suitable therefor.

Muteins in accordance with the present invention include proteins encoded by a nucleic acid, such as DNA or RNA, which hybridizes to DNA or RNA, which encodes an IL-18BP or encodes a viral IL-18BP, in accordance with the present invention, under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., (1987, 1992), and Sambrook et al., supra. Without limitation, examples of stringent conditions include washing conditions 12-20° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1×SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Any such mutein preferably has a sequence of amino adds sufficiently duplicative of that of an IL-18BP, or sufficiently duplicative of a viral IL-18BP, such as to have an activity comparable to IL-18BP. One activity of IL-18BP is its capability of binding IL-18. As long as the mutein has substantial binding activity to IL-18, it can be used in the purification of IL-18, such as by means of affinity chromatography, and thus can be considered to have substantially similar activity to IL-18BP. Thus, it can be determined whether any given mutein has substantially the same activity as IL-18BP by means of routine experimentation comprising subjecting such a mutein, e.g., to a simple sandwich competition assay to determine whether or not it binds to an appropriately labeled IL-18, such as radioimmunoassay or ELISA assay.

In one embodiment, any such mutein has at least 40% identity or homology with the sequence of either an IL-18BP or a virally-encoded IL-18BP homologue, as defined in WO 99/09063. More preferably, it has at least 50%, at least 60%, at least 70%, at least 80% or, most preferably, at least 90% identity or homology thereto.

Muteins of IL-18BP polypeptides or muteins of viral IL-18BPs, which can be used in accordance with the present invention, or nucleic acid coding therefor, include a finite set of substantially corresponding sequences as substitution peptides or polynucleotides which can be routinely obtained by one of ordinary skill in the art, without undue experimentation, based on the teachings and guidance presented herein. Preferred changes for muteins in accordance with the present invention are what are known as "conservative" substitutions. Conservative amino acid substitutions of IL-18BP polypeptides or proteins or viral IL-18BPs, may include synonymous amino adds within a group which have sufficiently similar physicochemical properties that substitution between members of the group will preserve the biological function of the molecule. It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention. Such synonymous amino add groups are set forth in Table 1, Table 2 and Table 3, below.

TABLE 1

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE 2

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE 3

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |

TABLE 3-continued

Most Preferred Groups of Synonymous Amino Acids

| Amino Acid | Synonymous Group |
|---|---|
| Glu | Glu |
| Met | Met, Ile, Leu |
| Trp | Met |

Examples of production of amino add substitutions in proteins which can be used for obtaining muteins of IL-18BP polypeptides or proteins, or muteins of viral IL-18BPs, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

In one embodiment, the inhibitor is a fused protein. The term "fused protein" refers to a polypeptide comprising an IL-18BP, or a viral IL-18BP, or a mutein or fragment thereof, fused with another protein, which, e.g., has an extended residence time in body fluids. An IL-18BP or a viral IL-18BP, may thus be fused to another protein, polypeptide or the like, e.g., an immunoglobulin or a fragment thereof.

"Functional derivatives" as used herein refers to derivatives of IL-18BPs or a viral IL-18BP, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of IL-18BP, or viral IL-18BPs, and do not confer toxic properties on compositions containing it. These derivatives may, for example, include polyethylene glycol side-chains, which may mask antigenic sites and extend the residence of an IL-18BP or a viral IL-18BP in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocydic aroyl groups) or O-acyl derivatives of free hydroxyl groups (for example that of seryl or threonyl residues) formed with acyl moieties.

As "active fractions" of an IL-18BP, or a viral IL-18BP, muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to IL-18BP.

In one embodiment, the inhibitor of IL-18 is a neutralizing antibody directed against IL-18 or its receptor, IL-18R. Preparation and use of such a neutralizing antibody against IL-18 is known in the art, such as that described in U.S. Patent Publication 20040141964. Neutralizing antibodies directed to any of the IL-18R subunits, may be used in accordance with the present invention. Such neutralizing antibodies against IL-18 are known in the art, such as described in U.S. Patent Publication 20130034569. The antibodies according to the invention may be polyclonal or monoclonal, chimeric, humanized, or even fully human. Recombinant antibodies and fragments thereof are characterized by high affinity binding to IL-18 or IL-18R in vivo and low toxicity. Neutralizing antibodies are readily raised in animals such as rabbits, goat or mice by immunization with IL-18 or IL-18R α or β. Immunized mice are particularly useful for providing sources of B cells for the manufacture of hybridomas, which in turn are cultured to produce large quantities of anti-IL-18 monoclonal antibodies.

Chimeric antibodies are immunoglobulin molecules characterized by two or more segments or portions derived from different animal species. Generally, the variable region of the chimeric antibody is derived from a non-human mammalian antibody, such as murine monoclonal antibody, and the immunoglobulin constant region is derived from a human immunoglobulin molecule. Preferably, both regions and the combination have low immunogenicity as routinely determined. Humanized antibodies are immunoglobulin molecules created by genetic engineering techniques in which the murine constant regions are replaced with human counterparts while retaining the murine antigen binding regions. The resulting mouse-human chimeric antibody preferably have reduced immunogenicity and improved pharmacokinetics in humans. In one embodiment, the IL-18 or IL-18R neutralizing antibody is a humanized antibody. An examples of humanized anti-IL-18 antibodies is described in the European Patent Application EP 0 974 600. In one embodiment, the neutralizing antibody is fully human. Fully human antibodies and methods for their production are known in the art. The technology for producing human antibodies is described in detail e.g. in WO00/76310, WO99153049, U.S. Pat. No. 6,162,963 or AU5336100.

Another example of the inhibitor of IL-18 is an immunoglobulin fusion, i.e. the inhibitor of IL-18 is a fused protein comprising all or part of an IL-18 binding protein, which is fused to all or a portion of an immunoglobulin. Methods for making immunoglobulin fusion proteins are well known in the art, such as the ones described in WO 01/03737, for example. The person skilled in the art will understand that the resulting fusion protein of the invention retains the biological activity of IL-18BP, in particular the binding to IL-18. The fusion may be direct, or via a short linker peptide which can be as short as 1 to 3 amino acid residues in length or longer, for example, 13 to 20 amino add residues in length. Said linker may be a tripeptide of the sequence E-F-M (Glu-Phe-Met), for example, or a 13-amino add linker sequence comprising Glu-Phe-Gly-Ala-Gly-Leu-Val-Leu-Gly-Gly-Gln-Phe-Met (SEQ ID NO: 11) introduced between the IL-18BP sequence and the immunoglobulin sequence. The resulting fusion protein has improved properties, such as an extended residence time in body fluids (half-life), increased specific activity, increased expression level, or the purification of the fusion protein is facilitated.

IL-18BP can be fused to the constant region of an Ig molecule, such as the heavy chain regions, like the CH2 and CH3 domains of human IgG1, for example. The generation of specific fusion proteins comprising IL-18BP and a portion of an immunoglobulin are described in example 11 of WO 99/09063, for example. Other isoforms of Ig molecules are also suitable for the generation of fusion proteins according to the present invention, such as isoforms IgG2, IgG4, or other Ig classes, like IgM or IgA, for example. Fusion proteins may be monomeric or multimeric, hetero- or homo-multimeric.

Administration

The pharmaceutical compositions of the present invention may be administered in a number of ways depending upon whether local or systemic treatment is desired. For systemic treatment, both enteral (e.g., oral) and parenteral (e.g., intravenous) administration are envisioned. The route of administration may be intravenous (I.V.), intramuscular (I.M.), subcutaneous (S.C.), intradermal (I.D.), intraperitoneal (I.P.), intrathecal (I.T.), intrapleural, intrauterine, rectal, vaginal, topical, intratumor and the like. The compounds of the invention can be administered by injection or by gradual infusion over time and can be delivered by peristaltic means. Parenteral administration includes intravenous drip, subcutaneous, intraperitoneal or intramuscular injection, pulmonary administration, e.g., by inhalation or insufflation.

Administration may be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays, for example, or using suppositories. For oral administration, the compounds of the invention are formulated into conventional oral administration forms such as capsules, tablets and tonics.

In one embodiment, administration results in contacting of the target HSPCs (e.g., HSPCs within the donor prior to donation, or HSPCs in the transplant recipient subject) with an effective amount of the inhibitor.

Therapeutic Pharmaceutical Compositions

Another aspect of the invention relates to therapeutic compositions comprising the inhibitor of IL-18 formulated for administration as described herein, formulated with a pharmaceutically acceptable carrier. In one embodiment, the composition comprises the IL-18 inhibitor and the HSPC to be administered to a subject.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The therapeutic compositions of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. Precise amounts of active ingredient required to be administered depend on the judgment of the practitioner and are peculiar to each individual.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means ±1%.

In one respect, the present invention relates to the herein described compositions, methods, and respective component(s) thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

The contents of all patents, patent applications, and publications identified in this application are incorporated herein by reference as they relate to the embodiments of the invention discussed in conjunction with their citation. All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention may be as defined in any one of the following numbered paragraphs.

1. A method for enhancing hematopoietic reconstitution of a subject in need thereof comprising:
   a) administering to the subject hematopoietic stem/progenitor cells (HSPC); and
   b) administering to the subject a therapeutically effective amount of an inhibitor of interleukin 18 (IL-18) to thereby inhibit IL-18 interaction with IL-18R molecules present on the HSPC administered in step a).
2. The method of paragraph 1, wherein administering step b) is by a route selected from the group consisting of enteral and parenteral.
3. The method of any one of paragraphs 1-2, wherein administering step b) is performed immediately after administering step a).
4. The method of any one of paragraphs 1-2, wherein administering step b) is performed prior to and immediately after administering step a).
5. The method of any one of paragraphs 1-4, wherein the inhibitor of IL-18 is administered to the subject over a period of time from about 1 day to 100 days directly after administration of the HSPCs.
6. The method of paragraph 5, wherein the period is from about 1 day to about 21 days directly after administration of the HSPCs.
7. The method of paragraph 5, wherein the period is from about 1 day to about 5 days directly after administration of the HSPCs.
8. The method of any one of paragraphs 5-6, wherein the period is about 5 days directly after administration of the HSPCs.
9. The method of any one of paragraphs 1-8, wherein the HSPCs are allogenic.
10. The method of any one of paragraphs 1-8, wherein the HSPCs are autologous.
11. The method of any one of paragraphs 1-10 wherein the HSPC are obtained from a donor subject treated with an inhibitor of IL-18 prior to harvest of the HSPCs to thereby expand early hematopoietic progenitor cells in the HSPCs.
12. A method for enhanced hematopoietic reconstitution in a subject in need thereof comprising administering to the subject hematopoietic stem/progenitor cells (HSPC) obtained from a donor subject, wherein the donor subject was treated with an inhibitor of interleukin 18 (IL-18) to thereby expand early hematopoietic progenitor cells prior to harvest of the HSPCs from the donor.
13. The method of any one of paragraphs 11-12, wherein the donor subject is treated with the inhibitor of IL-18 for a period of from about 1 day to about 10 days directly prior to harvest of the HSPCs.
14. The method of paragraph 13, wherein the period is from about 1 day to about 5 days directly prior to harvest of the HSPCs.
15. The method of any one of paragraphs 13-14, wherein the period is about 5 days directly prior to harvest of the HSPCs.
16. The method of any one of paragraphs 11-15, wherein the treatment of the donor subject is by administration of the inhibitor of IL-18 to the donor subject by a method selected from the group consisting of enteral and parenteral.
17. The method of any one of paragraphs 1-16, wherein the HSPCs are obtained from bone marrow, blood, placenta, or umbilical cord of the donor.
18. The method of any one of paragraphs 1-17, wherein the inhibitor of IL-18 is selected from the group consisting of IL-18 binding protein, an antibody against IL-18, an antibody against an IL-18 receptor subunits, an inhibitor of the IL-18 signaling pathway, an antagonist of IL-18 which competes with IL-18 and blocks the IL-18 receptor, an inhibitor of caspase-1 (ICE), an IL-18 isoform, an IL-18 mutein, an IL-18 fused protein, an IL-18 functional derivative, an IL-18 active fraction, and an IL-18 circularly permutated derivative thereof inhibiting the biological activity of IL-18.

The invention is further illustrated by the following examples, which should not be construed as further limiting.

EXAMPLES

Example 1

Stem cell/progenitor niches are functional units that exemplify the critical role of heterologous cell interactions in tissue homeostasis and regeneration. Niche-derived signals control the balance between quiescence, self-renewal and differentiation of primitive cells and are essential for maintenance of the stem cell/progenitor pool throughout life of an organism. However, uncovering the molecular nature of these signals has been challenging, since previous studies defined putative niche cells at the level of relatively large cell populations and hence lacked specificity and resolution needed to interrogate a small niche cell subset which is intimately involved in stem cell/progenitor regulation[2].

The anatomic proximity between a niche cell and a stem cell/progenitor cell is at the heart of the spatial and regulatory organization of the niche[4]. By focusing on cells in close apposition to Drosophila germ cell stem cells, definitive experimental evidence for the niche hypothesis was provided. A similar 'proximity principle' was used to evaluate the mammalian bone marrow hematopoietic microenvironment. Analysis of single mesenchymal cells in close proximity to transplanted HSPCs defined a transcriptional landscape useful for cell isolation and definition of novel hematopoietic regulators in vivo.

Results

Previous studies have shown that mesenchymal cells and endothelial cells are central to the regulation of HSPC[6-12]. While clarification of the specific mesenchymal subsets involved in the stem cell niche continues, it is apparent that whether the cells are defined by leptin receptor, nestin, Prx1 or Mx-1 promoter activity, they do contribute to bone formation in vivo. These stem/progenitor cells, formally of osteolineage potential in vivo with some having broader multi-potential, appear to regulate primitive hematopoietic cells while more mature osteolineage cells (OLC) regulate lineage-specific progenitors. In the setting of transplantation, HSPCs appear to localize close to endosteum and the OLC populations resident there[13]. Transplanted HSCs home more closely to OLCs when compared to lineage-committed progenitors suggesting differential functional interactions[13]. It was hypothesized that rare HSPC-proximal OLCs are or become molecularly distinct from those located further away and are enriched for transcripts encoding niche-derived regulators of HSPC function. For the purpose of the study, OLCs were arbitrarily defined as located within two cell diameters of engrafted HSPC as "proximal OLCs", and those located greater than five cell diameters away defined as "distal OLCs".

To perform genome-wide unbiased comparative transcriptome analysis of proximal and distal OLCs, an experimental platform was designed which combined single cell RNA-Seq[14] with retrieval of individual OLCs directly from fresh unfixed sections of trabecular mouse bone (FIG. 1a). First, adult bone marrow lineage$^-$ kit$^+$ Sca1$^+$ (LKS) 34$^-$Flk2$^-$ cells were intravenously transplanted and fluorescently labeled with a lipophilic membrane-bound dye, DiI, into sublethally irradiated newborn col2.3GFP recipients; in this mouse strain, the majority of OLCs are labelled with GFP[15]. Forty-eight hours later, the animals were sacrificed and transverse vibratome sections of femur obtained. The majority of DiI-labelled cells were seen in the central marrow cavity, some forming clusters. However, in the endosteal area, very rare transplanted HSPCs were observed located in close proximity to individual OLCs and seen as singlets, implying that they remained quiescent (FIG. 1b). Using in situ enzymatic digestion and micropipette aspiration, individual proximal and distal OLCs were harvested for subsequent RNA-Seq analysis.

In total, eight proximal OLCs and eight distal OLCs were examined. As expected, transcript abundance in single-cell RNA-seq samples was found to exhibit a high degree of variability, likely originating from both technical noise and intrinsic biological stochasticity[6]. To accommodate such stochasticity, a probabilistic method was developed, which uses Bayesian approach to estimate the likelihood of expression magnitude based on the observed reads for that gene and the overall error characteristics within the transcriptome of that particular single cell sample—Single Cell Differential Expression (SCDE)[17]. By comparing combined probabilistic estimates from single cell transcriptomes of eight proximal OLCs and eight distal OLCs, the method estimated the likelihood that the level of expression of a given gene differed between the proximal and distal OLCs (Vcam-1 gene shown as a representative example, FIG. 2a).

Figure 2:
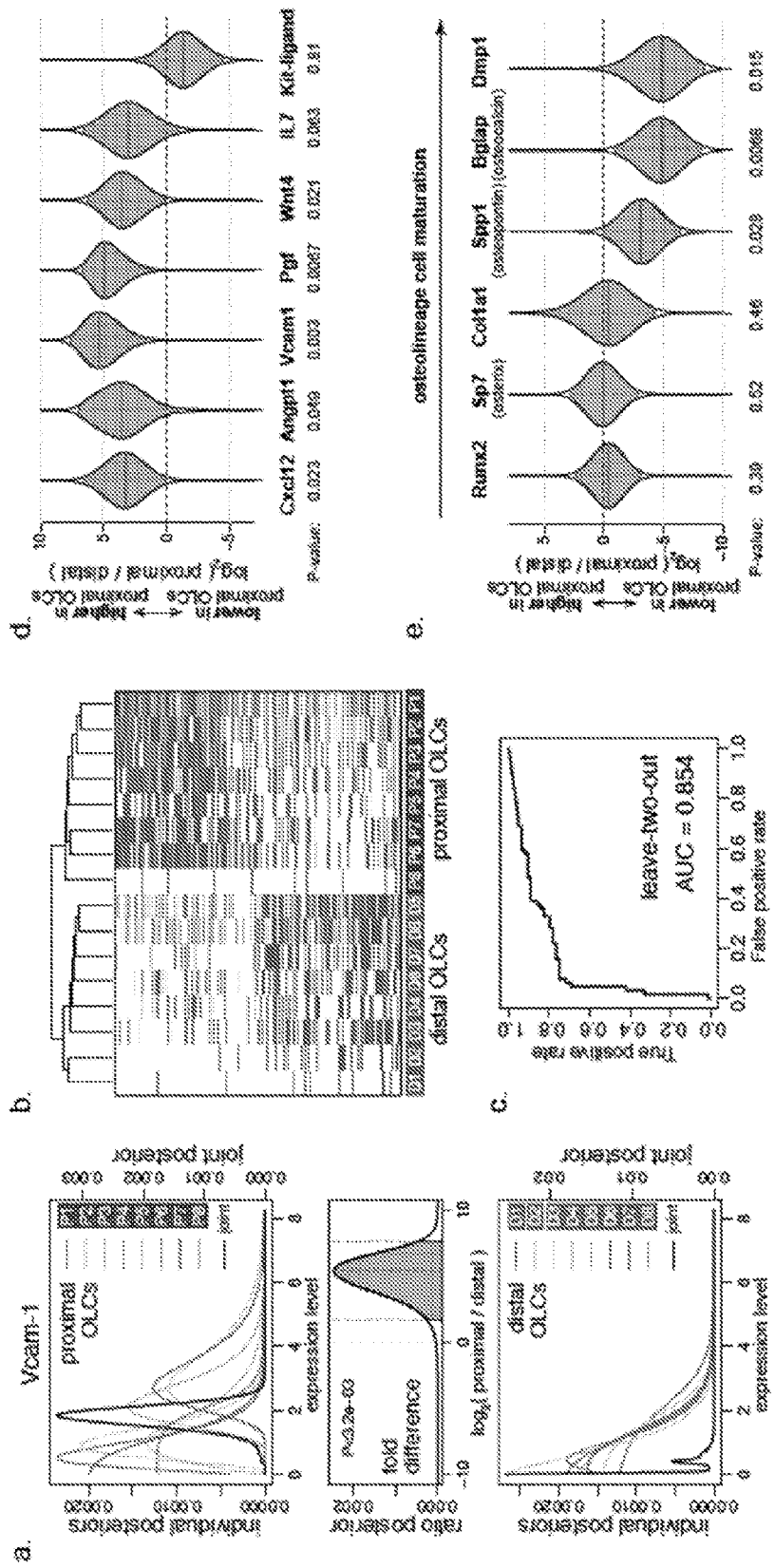
FIG. 2A-FIG. 2E shows experimental results which indicate HSPC-proximal cells are immature OLCs with a distinct transcriptional profile, enriched for known niche-derived HSPC regulators. A) To accommodate high levels of noise present in the single-cell measurements, a Bayesian approach was used to estimate the posterior distribution of expression levels based on the observations from each cell (colored lines, top and bottom panels). The joint posteriors (black lines) describe the overall estimation of likely expression levels within the HSPC-proximal (top) and distal (bottom) cells, and are used to estimate the posterior of the expression fold difference (middle plot). The shaded area under the fold-difference posterior shows 95% confidence region. Analysis of the Vcam-1 gene is shown as an example. B) Individual OLCs formed two clusters based on the top 200 differentially expressed genes. Each row represents a gene, with the most likely gene expression levels indicated by color (blue—high, white—low/absent). The expression level of each gene were scaled by the maximum expression level across all cells. C) An unbiased classification can distinguish HSPC-proximal and distal OLCs based on the overall transcriptome signature. The receiver-operator curve is shown for the Support Vector Machine classification where all successive pairs of cells (one proximal and one distal) were classified based on the training data provided by other cells. D) and E) HSPC-proximal cells are immature OLCs which display elevated expression of the genes previously shown to be functionally relevant within the HSPC niche. The violin plots show the posterior distribution of the expression fold-difference (y-axis, log 2 scale) for each gene, with the shaded area marking the 95% confidence region. The horizontal solid red lines show the most likely fold-change value. The P-values assessing significance of elevated expression in the HSPC-proximal OLCs are shown below each gene.

The expression levels of the top 200 differentially expressed genes are shown in FIG. 2b. While there is a high variability within individual samples, the profiles of proximal OLCs are clustered separately from the profiles of distal OLCs. To test whether there existed a stable transcriptional signature that differentiates the HSPC-proximal and distal OLCs, Support Vector Machine classifiers were constructed using a set of all detected transcripts. Using leave-two-out cross-validation strategy, pairs of HSPC-proximal and distal cells were iteratively excluded from the training set and the ability to classify the excluded cells was evaluated. The HSPC-proximal and distal cells were correctly classified in most cases (AUC=0.854, P<10$^{-5}$), illustrating that HSPC-proximal OLCs possess a distinct genome-wide transcriptional signature (FIG. 2c). The complete RNA-Seq dataset can be accessed via URL http://pklab.med.harvard.edu/sde/viewpost.html?dataset=olc.

Figure 5:
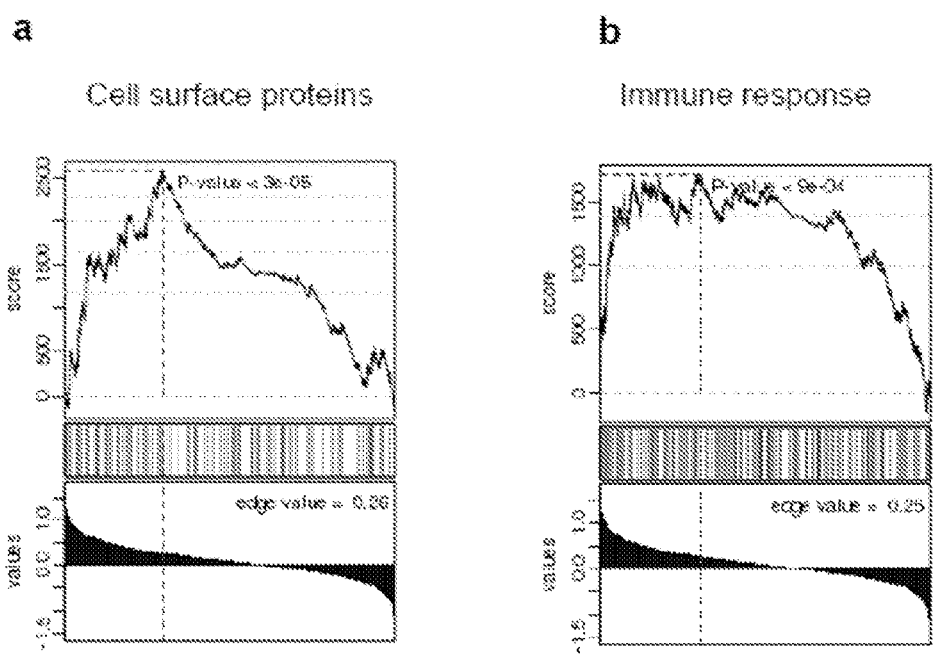
FIG. 5A-FIG. 5B show results of gene set enrichment analysis (GSEA) of differentially expressed genes between proximal and distal OLCs. A) Proximal cells demonstrated a significant enrichment for gene sets "Surface proteins", and B) "Immune response" (p<0.0005).

To initially validate single cell RNA-Seq data at the level of individual genes, the dataset was examined for differential expression of genes previously shown to be functionally relevant in the HSPC niche[18-23]. Of those transcripts that were detected, with the exception of Kit-ligand, proximal OLCs showed higher expression levels of niche-associated genes, most notably Cxcl12 and Vcam-1 (FIG. 2d). Further, gene set enrichment analysis of the differential expression between proximal and distal OLCs showed that proximal OLCs displayed a significant enrichment for genes encoding cell surface proteins and those involved in immune response, supporting the role of these cells in intercellular communications (FIG. 5). In keeping with previous observations about the identity of HSPC-supportive mesenchymal cells[12], proximal OLCs were found to possess an immature OLC signature, as evidenced by equal expression levels of genes denoting commitment to the osteoblast lineage (Runx2, osterix), but significantly lower levels of mature OLC markers (osteocalcin, osteopontin, Dmp1) (FIG. 2e). Thus, this technical and computational approach identified a molecularly distinct subset of immature OLCs, whose molecular signature was consistent with their putative regulatory role in the HSPC niche.

Next, whether detecting cell surface proteins corresponding to differentially expressed transcripts would enable the development of an antibody-based strategy for the identification and prospective isolation of an OLC population, which is comparable to micropipette-aspirated individual proximal OLCs, was explored. Based on the magnitude of expression difference and commercial availability of reagents, antibodies against VCAM-1 and Embigin, a transmembrane protein of the immunoglobulin superfamily class of cell adhesion molecules not previously described in the HSPC niche24 were used. Both of these molecules displayed significantly higher transcript abundance in proximal OLCs (FIGS. 2a and 3a). Using fluorescence-activated cell sorting (FACS), a rare (3%) subset of EmbiginhighVCAM-1+ cells among GFP+ CD45-Ter119– cells, were identified which were obtained from the long bones of adult non-irradiated col2.3GFP mice (FIG. 3b).

Figure 3:
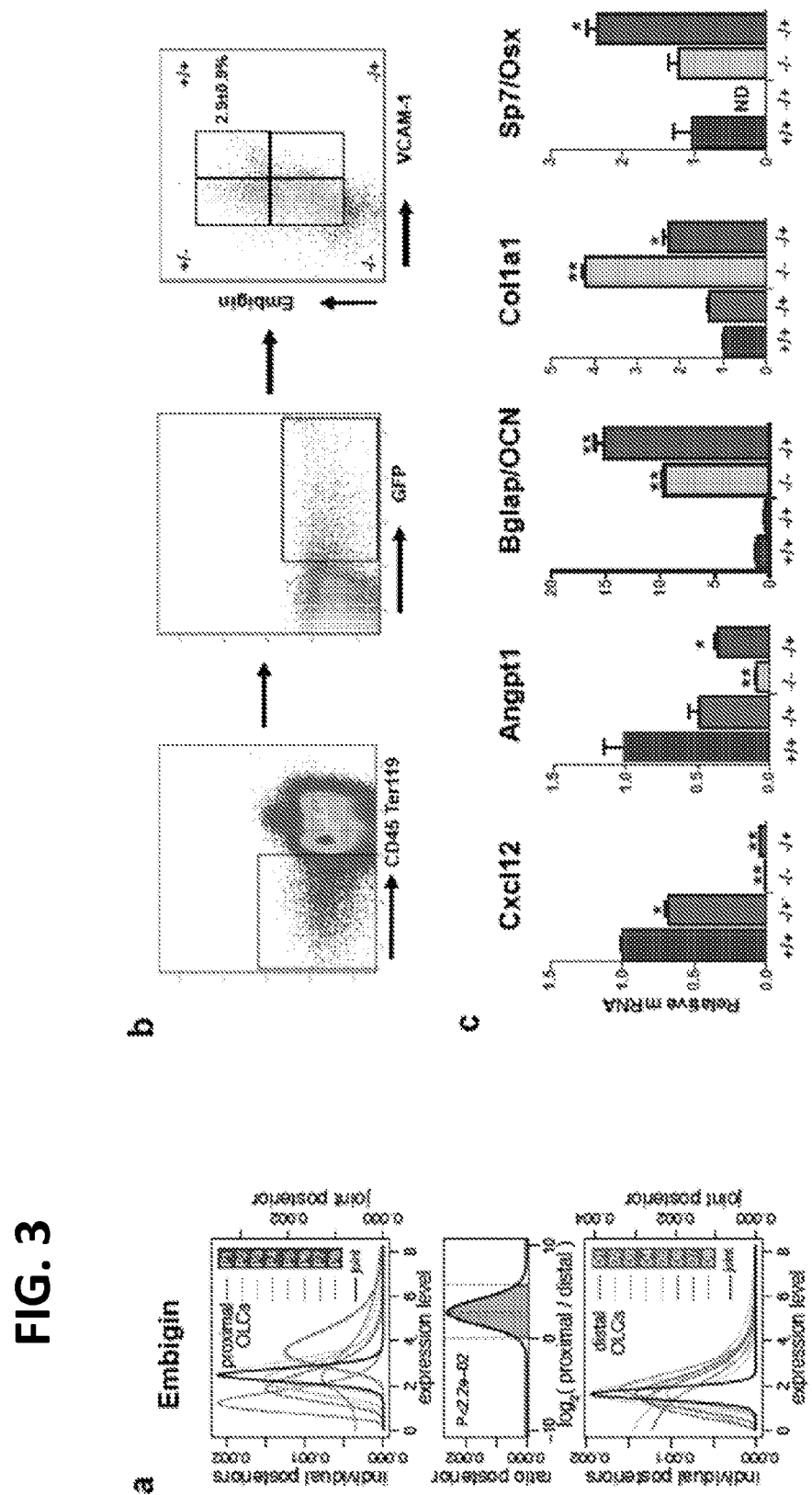
FIG. 3A-FIG. 3C show experimental results that indicate embigin and VCAM-1 mark a subset of osteolineage cells which are comparable to HSPC-proximal OLCs. A) Single-cell RNA-Seq data demonstrated elevated expression of Embigin in the HSPC-proximal OLCs. B) Single cell suspension was obtained from collagenase-treated long bones of adult col2.3GFP mice and analyzed by FACS. Four cell subsets within $CD45^-Ter119^-GFP^+$ fraction were FACS-sorted as follows: $Embigin^{high}$ $VCAM1^+$ (+1+), $Embigin^{low/neg}$ $VCAM1^+$ (−/+), $Embigin^{low/neg}$ $VCAM1^-$ (−/−) and $Embigin^{high}$ $VCAM1^-$ (+/−) and analyzed by real-time PCR analysis, as shown in C) *p<0.05, **p<0.01.

Real-time PCR analysis showed that compared to other col2.3GFP$^+$ cell subsets, Embigin$^{hi}$g$^h$VCAM-1$^+$ cells expressed higher levels of CXCL12 and angiopoietin 1, lower levels of osteocalcin and collagen 1 and were positive for osterix, thus recapitulating the expression pattern of these genes in micropipette-aspirated proximal OLCs (FIG. 3c). GFP$^+$Embigin$^{hi}$g$^h$VCAM-1$^+$ cells were isolated with a similar Q-PCR profile from newborn and adult animals that were lethally irradiated but non-transplanted (data not shown), indicating that these cells already existed in the bone marrow microenvironment. Collectively, these data provide in vivo validation of the RNA-Sect data at the protein level and demonstrate that this cell proximity-based approach can be used as a tool for the prospective isolation of a "proximal OLC"-comparable cell subset.

Finally, whether this approach could be used to identify novel non-cell autonomous hematopoietic regulators in vivo was investigated. Among the transcripts enriched in proximal OLCs, a statistically significant increase in interleukin-18 (IL18)3, a cytokine not previously thought to be functioning within the HSPC niche was noted (FIG. 4a). IL18 plays a role in promoting inflammation and angiogenesis and has been shown to act upstream of the known HSPC niche regulators CXCL12 and VCAM-125,26.

Analysis of IL18 receptor (IL18R1) expression by FACS revealed that it was not expressed in LKS CD34$^-$Flk2$^-$ long-term HSCs (LT-HSC), but was detectable in LKS CD34$^+$Flk2$^-$ short-term HSCs (ST-HSC) and LKS CD34$^+$ Flk2+ multi-potent progenitors (MPP) (FIG. 4b). No IL18R1 expression was observed in lineage-negative Sca1− c-kit+ progenitors.

Figure 6:
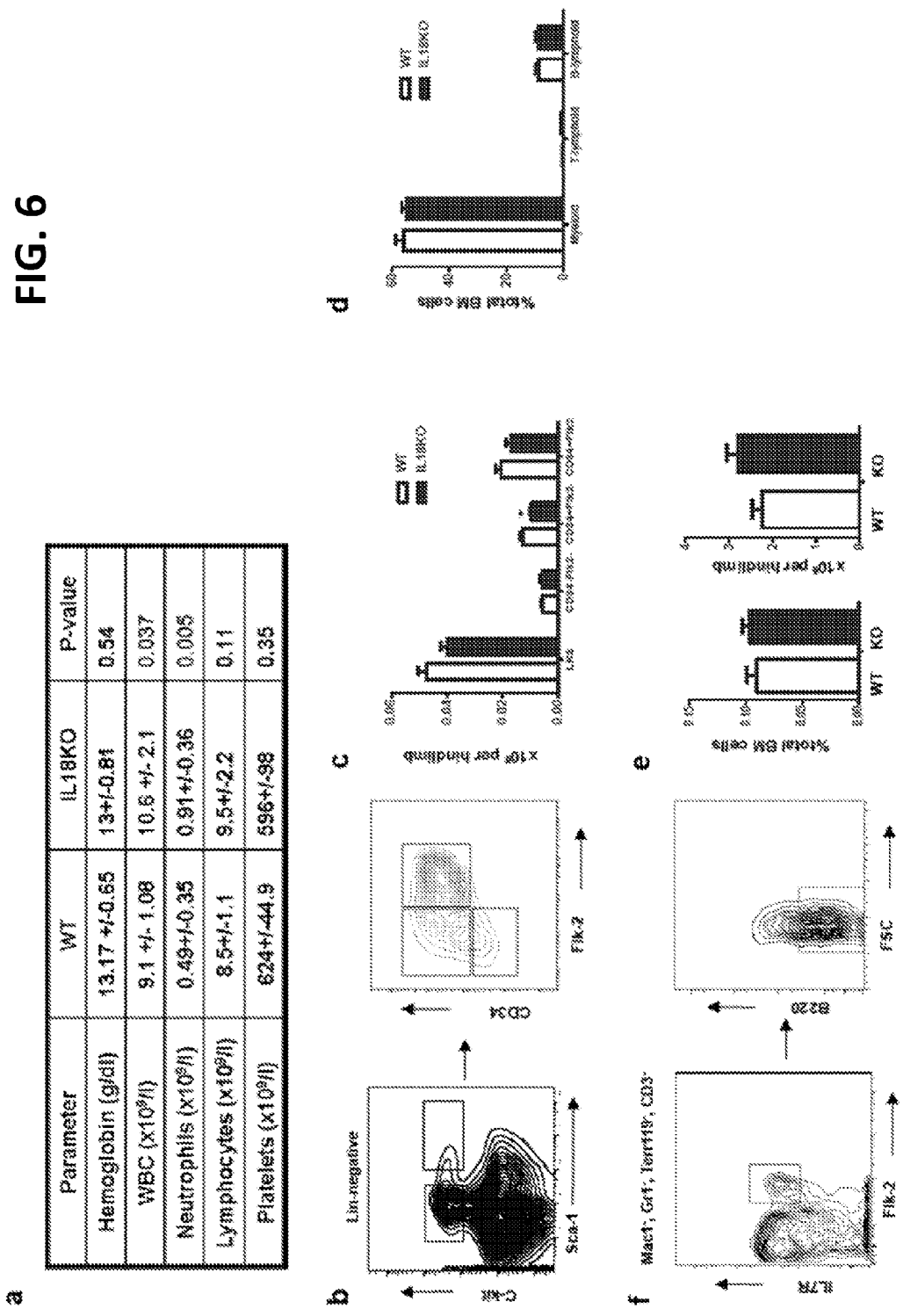
FIG. 6A-FIG. 6F show experimental results of analysis of hematopoietic parameters in IL18KO mice at the steady state. A) Peripheral blood analysis of IL18KO mice showed a slight increase in total WBC and neutrophils (*p<0.05, n=12 per group). B) FACS-gating strategy used for analysis of primitive hematopoietic subsets. C) IL18KO mice displayed a lower absolute number of LKS ST-HSCs (*p<0.05, n=12 per group). D) Normal multilineage differentiation in IL18KO mice (n=6 per group). E) Gating strategy for enumeration of common lymphoid progenitors (CLP). F) No difference was observed in frequency (left panel) and absolute number (right panel) of CLPs in IL18KO mice (n=7 per group).

Examination of peripheral blood of IL18KO mice 27 demonstrated no gross abnormalities apart from a modest neutrophilia (FIG. 6a). However, immunophenotypic quantification of primitive cell subsets revealed a moderate decrease in the frequency of total LKS cells, short-term HSCs and multipotent progenitors, while the frequency of LT-HSCs was unaffected, in accord with the expression pattern of IL18R1 (FIG. 4c). The same trend was observed when the absolute number of these cell populations was assessed, with a statistically significant decrease of ST-HSCs, but no effect on multilineage differentiation (FIG. 6b-d). Given the recent data on the role of the bone marrow niche in maintenance of primitive lymphoid cells 9,11, common lymphoid progenitors in IL18KO mice were enumerated, but no significant difference in the frequency or the absolute number was found (FIG. 6e).

Next, whether the reduction in primitive hematopoietic cell subsets was due to an effect of IL18 on quiescence was assessed. Cell cycle analysis using Ki-67/Hoechst staining showed that in IL18KO mice, there was a notable decrease in the proportion of LKS CD34+ cells in the G0 phase and a corresponding increase in the S/G2/M phase, while no changes were detectable in LKS CD34-cells (FIG. 4d). These experiments demonstrated that the IL18-IL18R1 signaling pathway is involved in maintenance of cellular quiescence, which appears to selectively regulate early hematopoietic progenitors.

Figure 7:
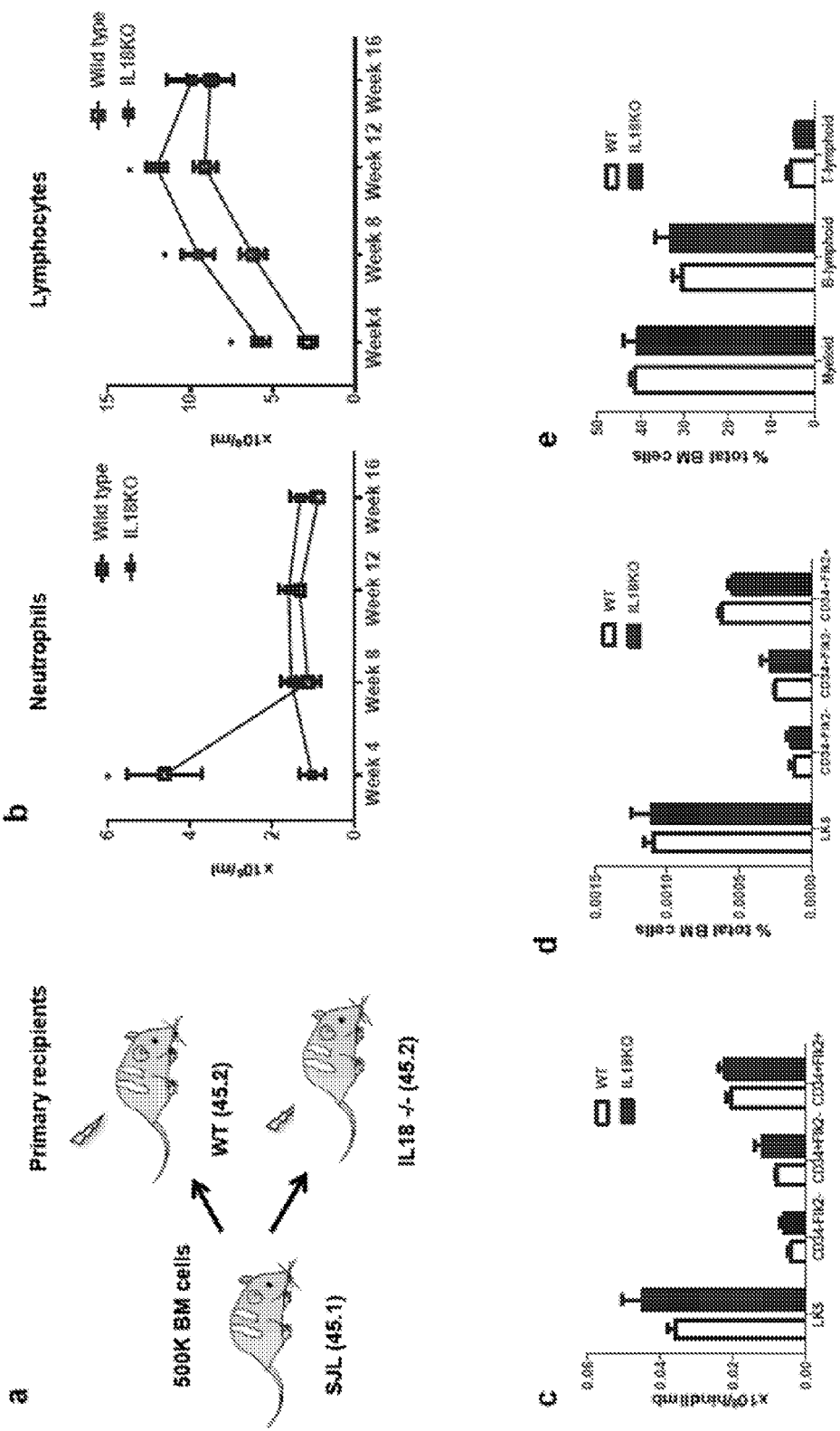
FIG. 7A-FIG. 7E show experimental results of analysis of post-transplant reconstitution in primary IL18KO recipients. A) Experimental design. B) Peripheral blood analysis during 16 weeks post-transplant showed a lymphoid bias during weeks 4-12 (*p<0.05, n=4-7 per group). The experiment was repeated with similar results. C), D), and E) At 16 weeks post-transplant, analysis of the bone marrow showed no difference in the absolute number, frequency of primitive hematopoietic cells and multilineage reconstitution between IL18KO and WT recipients.
Figure 8:
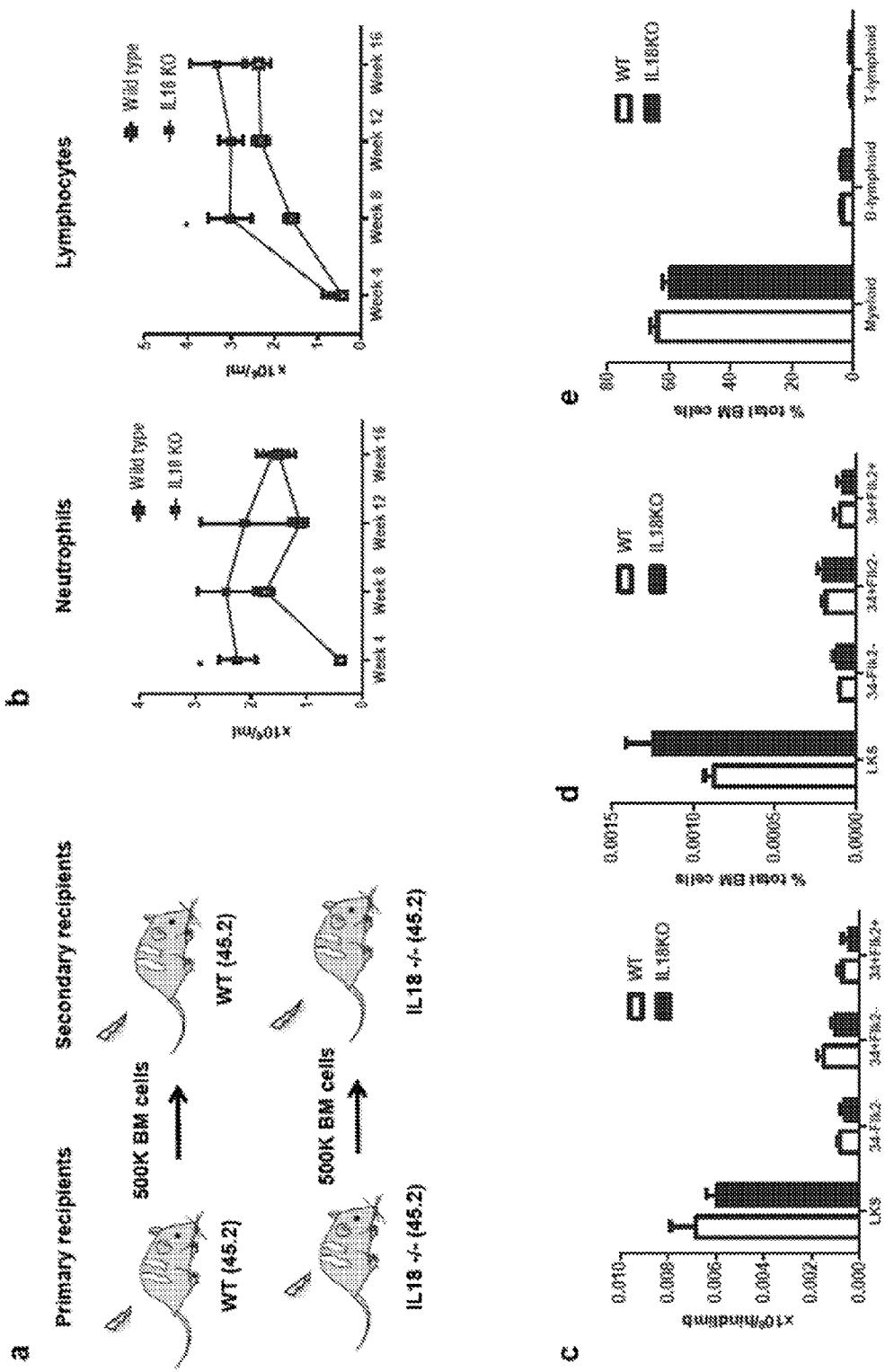
FIG. 8A-FIG. 8E show experimental results of analysis of post-transplant reconstitution in secondary IL18KO recipients. A) Experimental design. B) Peripheral blood analysis during 16 weeks post-transplant showed a lymphoid bias at week 8 (*p<0.05, n=5-7 per group). C), D), and E) At 16 weeks post-transplant, analysis of the bone marrow showed no difference in the absolute number, frequency of primitive hematopoietic cells and multilineage reconstitution between IL18KO and WT recipients.
Figure 9:
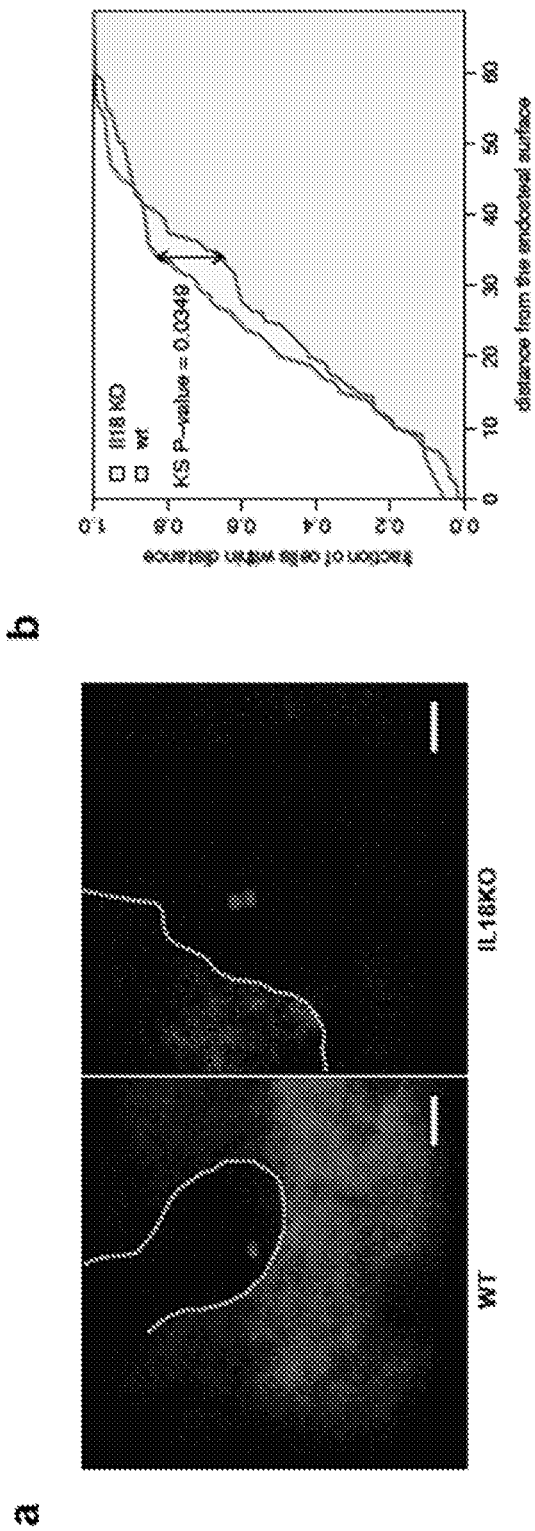
FIG. 9A-FIG. 9B show experimental results of in vivo imaging of transplanted WT LKS cells demonstrates faster proliferation and localization further away from endosteal surface in IL18KO recipients. A) tdTomato+WT LKS cells injected into lethally irradiated WT or IL18KO recipients were imaged 24 hours after transplantation. Representative in vivo images of calvarial bone marrow are shown (blue-bone signal, broken line—endosteal surface). B) The shortest three-dimensional distance between $tdTomato^+$ cells and the endosteal surface was calculated. Kolmogorov-Smirnov test P-value is shown.

To investigate whether the above effect was due to the IL18 production by the bone marrow microenvironment, WT bone marrow (CD45.1) was transplanted into lethally irradiated IL18KO or WT recipients (CD45.2). Both in primary and secondary transplants, IL18KO recipients displayed faster hematopoietic reconstitution, however this effect was transient, suggesting that the absence of IL18 in the recipient animals predominantly affected short-term repopulating cells, particularly those with lymphoid potential (FIG. 4e, FIG. 7a, b and FIG. 8a, b). In keeping with this, bone marrow examination at 16 weeks (a time at which reconstitution is provided by LT-HSC) showed that both primitive and mature cell subsets were present at the same number and frequency (FIG. 7c-e and FIG. 8c-e). To investigate the effect of IL18 deletion in the bone marrow microenvironment on early post-transplant progenitor expansion, in vivo imaging studies were performed using two-photon confocal microscopy[13]. Equal numbers of tdTomato+ LKS cells were transplanted from MTMG mice[28] into lethally irradiated IL18KO or WT recipients. Twenty-four hours later, a higher number of tdTomato+ cells were found in the calvarial bone marrow of IL18KO recipients, predominantly due to a greater proportion of cell doublets, suggesting faster proliferation of transplanted LKS cells (FIG. 4f and FIG. 9a). Notably, these changes were associated with a lower proportion of cells localizing within 20-40 μm from the endosteal surface—the area which would normally be occupied by transplanted hematopoietic progenitors (FIG. 4g and FIG. 9b)[13]. These observations suggest that increased proliferation of transplanted LKS cells in the IL18-deficient microenvironment is also associated with altered localization.

This work demonstrates the development and validation of an approach, in which the proximity between a single transplanted HSPC and an individual mesenchymal cell was used as a sole criterion for defining the transcriptional landscape within a bone marrow niche. It shows that HSPC-proximal OLCs have a distinct genome-wide transcriptional profile; moreover, they preferentially express several known niche-derived HSPC regulators, indicating that had these molecules not been previously identified, this approach would have suggested them. One notable exception was kit-ligand/stem cell factor, however, this is consistent with the recent data that OLCs are not a major source of this molecule 9.

Further, this approach enabled the identification of a novel set of cell surface markers (Embigin and VCAM-1), which were successfully used to prospectively isolate a "proximal OLC"-comparable population from the long bones of adult col2.3GFP+ mice. While investigating the function of this rare cell population will require cell or cell-specific gene ablation studies, the data and the expression of CXCL12 and VCAM1 suggest that it may be involved in regulation of HSPC quiescence and retention in the niche.

Finally, the utility of the approach was demonstrated to identify novel non-cell autonomous hematopoietic regulators. Using gene deletion studies, 8 was shown to act as anon-cell autonomous hematopoietic regulator in vivo. While this finding came from the study of OLCs, the possibility that other cellular components of the bone marrow niche which are known to express this molecule (such as osteoclasts and macrophages) contribute to its effect in-vivo cannot be excluded[29-32]. IL18 was found to promote quiescence in short-term repopulating cells (ST-HSCs and MPPs). The apparent selectivity of the effect of IL18 on short-term repopulating cells, in particular the absence of LT-HSC exhaustion after primary and secondary transplantation into IL18KO recipients, suggests that transient inhibition of IL18-IL8R1 might be worthy of study to accelerate early post-transplant hematopoietic reconstitution without depleting LT-HSCs.

In aggregate, our studies demonstrate the feasibility and the power of using a proximity-based single cell approach in deciphering the molecular pathways that govern heterologous cell interactions in vivo.

Materials and Methods

Mice.

Wild-type C57B16, MTMG[28], IL18KO and IL18R1KO[27] mice were obtained from the Jackson laboratory. Col2.3GFP mice were previously described[15].

Single OLC Harvesting and RNA-Seq.

Newborn col2.3GFP animals were injected with DiI-labeled LKS CD34−Flk2− adult bone marrow cells, as described below, and sacrificed 48 hours after transplantation. Femurs were dissected, embedded in 10% low melting temperature agarose (Lonza) and sectioned at 100 p. using a vibratome (Leica). Single OLC harvesting was performed using a physiology microscope BX51 (Olympus) equipped with filters to detect GFP and DiI fluorescence, DIC optics, micromanipulators (Eppendorff), real-time imaging camera, peristaltic pump, in-line heater, perfusion chamber (Harvard Apparatus) and SAS Air Syringe (Research Instruments). Sections were pre-screened for the presence of rare GFP-labeled OLCs located next to single DiI-positive transplanted HSCPs, which were found in 1-2 out of 15 sections per animal. Once a target proximal OLC was identified, the section was rotated so that the target was directly opposite the aspiration pipette (Humagen) and secured against the bottom of the perfusion chamber using a horizontal portion of the holding pipette (Humagen). With the aspiration pipette just above the target, the section was perfused with warm (37 C) cell dissociation solution (Liberase TM, Roche) for 8-10 minutes while the target cell was visually monitored. Then, applying positive pressure from the micropipette using Air Syringe, hematopoietic cells surrounding the target OLC were dislodged to create a 20-30 p. clearing. Finally, the aspiration pipette was lowered onto the target OLC, the cell was gently detached from the endosteal surface and aspirated. The presence of GFP fluorescence in the aspirated cell inside the aspiration pipette was confirmed, the contents of the pipette was ejected into a PCR tube with the lysis buffer for the single cell RNA-Seq protocol, and frozen immediately at −80 C. Reverse transcription, cDNA amplification, library preparation and SOLiD RNA-Seq were performed as described[14].

FACS Analysis.

Whole bone-marrow mononuclear cells (BMMNC) were collected by crushing tibias, femurs and hips and stained with the following monoclonal antibodies: c-Kit APC, CD34 FITC (e-Bioscience), Sca1 BV421, Flk2 PE, IL18Rα/CD218a (Biolegend), CD48 APCCy7 (BD), lineage cocktail biotin (B220, Mac1, Ter119, CD3, CD4, CD8 at 1:1:1:1:1:1) followed by streptavidin Pacific Orange (Invitrogen). LT-HSCs, ST-HSCs and MPP were gated as described[33]. For the lineage analysis, red cell-depleted BMMNC or peripheral blood samples were stained with CD3 APC (e-Bioscience), Mac1FITC, Gr1 PeCy7 and B220-PE (BD). For CLP analysis[34], BMMNC were stained with FITC-conjugated antibodies against Mac1, Gr1, CD19, Ter119, CD3 Pacific Blue, Flk2 PE, B220 PE Cy7 and biotin-conjugated IL7R/CD127, followed by streptavidin PerCP Cy5.5 (all from BD). For post-transplant chimerism analysis, CD45.1 AF700 and CD45.2 Pacific Blue (BD) were added. 7-AAD (BD) or DAPI (Invitrogen) were used as viability dyes. At least $2\times10^6$ events per sample were acquired for progenitor analysis and $10^4$ events for lineage analysis using a BD LSRII flow-cytometer.

For cell cycle analysis, BMMNC were lineage-depleted using biotin-conjugated antibodies for lineage-specific markers and streptavidin-conjugated microbeads on Miltenyi column and stained with monoclonal antibodies for HSPC markers, as described above. The cells were permeabilized using Cytofix/Cytoperm Fixation/Permeabilization Kit (BD) according to the manufacturer's instructions and stained with Ki-67 FITC (BD) and Hoechst 33342 (Invitrogen).

For FACS analysis/sorting of osteolineage cells, bone fragments were obtained by gently crushing tibiae, femora, humeri and pelvic bones of 6-8 weeks old col2.3GFP mice. After rinsing away the bone marrow cells, the fragments were incubated with 0.25% Collagenase (Stem Cell Technologies) at 37° C. with gentle agitation for 1 hour. The samples were vortexed several times during the incubation, then filtered through 0.45 micron mesh and stained with CD45 APC Cy7, Ter 119 APC Cy7 (BD), Embigin PE (E-Bioscene) and CD106-APC (R&D Systems). The samples' were analysed using LSRII (BD) or FACS-sorted using Aria (BD). Compensation and data analysis were performed using Flowjo 7.6 software.

Bone Marrow/Stem Cell Transplantation.

Adult recipients (CD45.2) were irradiated 950 cGy the evening before and transplanted with 500K total bone marrow cells (CD45.1) via retro-orbital injection. For serial transplantation, equal number of cells from each recipient was pooled, and secondary recipients (CD45.2) were injected with 500K cells per animal. Recipients' peripheral blood chimerism was assessed 4, 8, 12 and 16 weeks after transplantation.

For neonatal transplantation, col2.3GFP P2 pups were irradiated 450 cGy the evening before 35. Adult bone marrow LKS 34⁻Flk2⁻ cells were isolated as described and labeled with DiI according to manufacturer's instructions. 5000-7000 cells per animal were injected in a 50 μl volume via anterior facial vein, as described[36].

Bioinformatics and Statistical Analysis.

The differential expression estimates were obtained from single-cell RNA-seq data using the approach described in Kharchenko et al.[17] The stability of differential expression signature distinguishing OLC-proximal and distal cells was tested using support vector machine (SVM) classifier as follows: the SVM classifiers were constructed using all genes for which expression was detected in any of the examined cells; the ability to distinguish OLC-proximal and distal cells was tested using leave-two-out validation: one OLC-proximal and one OLC-distal cell was excluded, and a v-classification SVM was constructed based on all remaining cells using e1071 R package. All possible pairs of OLC-proximal and distal cells were tested to evaluate the classification performance (FIG. 2C).

Intravital Microscopy.

WT C57B16 mice or IL18KO mice were irradiated 950 cGy the night before and were intravenously injected with 50,000 LKS cells obtained from MTMG mice (for tdTomato labeling). Intravital imaging of calvarial bone marrow and data analysis were performed at 24 hours post-transplant, as previously described[13].

Real Time PCR.

RNA extraction was performed using PicoPure kit (Arcturus/Life Technologies). Reverse transcription was done using Superscript III RNA polymerase (Invitrogen), according to manufacturer's instruction. SYBR-Green real-time PCR and relative quantification were performed using Primer Plus thermocycler (Life Technologies). The annealing temperature for all primer pairs was 60'C. The following primer sequences were used: GAPDH Fw ATG AAT ACG GCT ACA GG (SEQ ID NO: 1), GAPDH Rev CTC TTG CTG AGT GTC CTT GCTG (SEQ ID NO: 2), CXCL12 Fw CAA CAC TCC AAA CTG TGC CCT TCA (SEQ ID NO: 3), CXCL12 Rev TCC TT GGG CTG TTG TGC TTA CT (SEQ ID NO: 4), Osx Fw CCT TGT ACC ACG AGG ATA GG (SEQ ID NO: 5), Osx Rev CCC ACC CTT CCC TCA CTC AT (SEQ ID NO: 6), Col1 Fw GTA TCT GCC ACA ATG GCA CG (SEQ ID NO: 7), Col1 Rev CTT CAT TGC ATT GCA CGT CAT (SEQ ID NO: 8), Ocn Fw CCA TCT TTC TGC TCA CTC TGC (SEQ ID NO: 9), Ocn Rev TGG ACA TGA AGG CTT TGT CA (SEQ ID NO: 10).

Example 2

Competitive Transplant Comparing the Reconstitution of Kinetics of WT and IL18 Receptor Knock-Out Bone Marrow Cells Post-transplant bone marrow aplasia is a major cause of morbidity and mortality after bone marrow transplant (BMT) Enhancing proliferation of short-term repopulating progenitors is an attractive strategy to accelerate post-transplant hematopoietic recovery, since the early reconstituting ability of these cells appears to be superior to that of long-term HCSs (LT-HSC). However, previously characterized extrinsic molecular pathways governing kinetics of short-term repopulating cells are also known to control LT-HSCs, raising a concern that manipulating those pathways in the transplant setting may lead to LT-HSC exhaustion.

Interleukin-18, a pro-inflammatory cytokine, was previously identified as a novel non-cell autonomous regulator of quiescence, which appears to selectively regulate short-term progenitors. IL18 receptor was not expressed in long-term HSCs, but was present in ST-HSCs and multi-potent progenitors; in IL18KO mice, a greater proportion of these cells were in S/G2/M phase of cell cycle, while the kinetics of LT-HSCs were unchanged. Notably, IL18KO recipients of WT bone marrow displayed faster peripheral blood lymphoid recovery during weeks 4-12 (both in primary and secondary transplants), while no changes in LT-HSC frequency and absolute number at 16 weeks post-transplant were detected.

Figure 10:
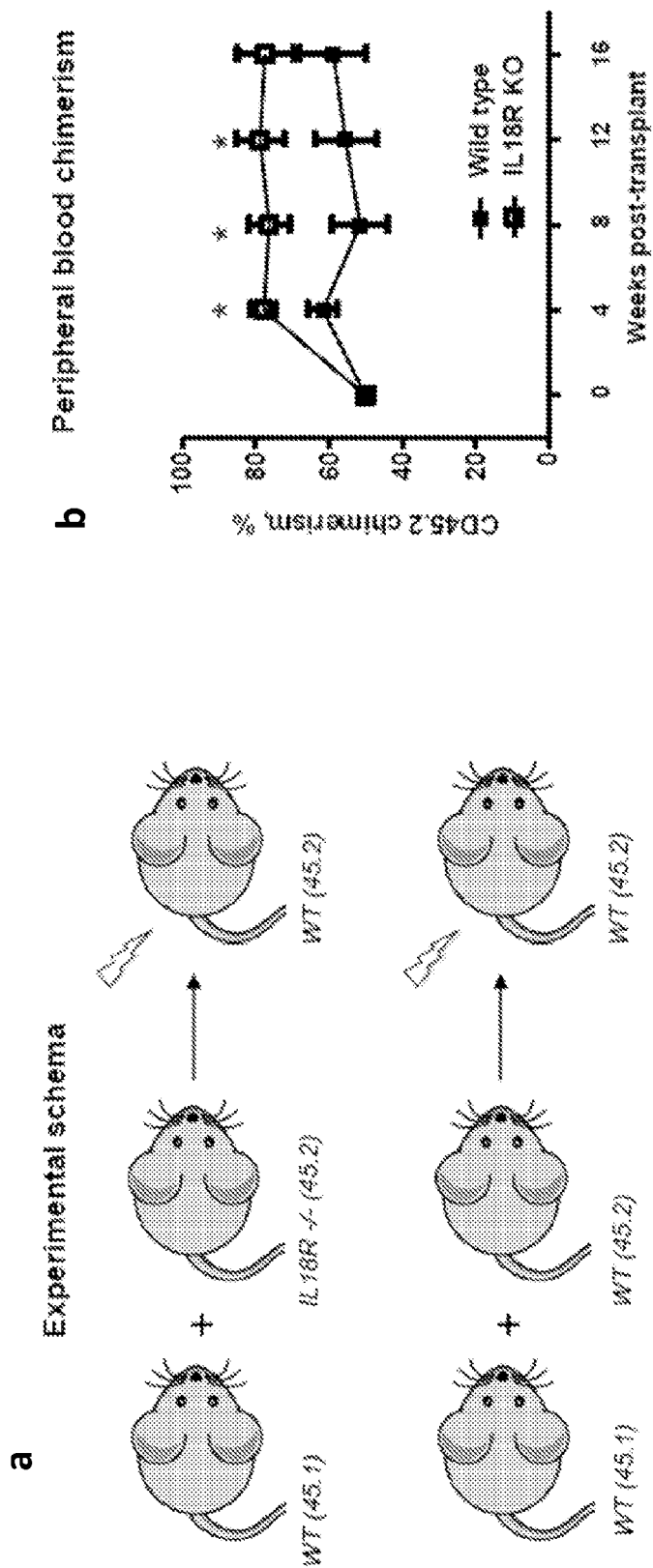
FIG. 10A-FIG. 10B show experimental results of competitive transplant comparing the reconstitution kinetics of WT and IL18 receptor knock-out bone marrow cells. A) shows the experimental schema. B is a graphical representation of the data obtained.

In this experiment, the ability of CD45.2 IL18R KO bone marrow cells to compete with CD45.1 WT cells was compared to the ability of CD45.2 WT cells to compete with CD45.1 WT cells. The results are shown in FIG. 10. Between weeks 4-12, CD45.2 IL18R KO cells were better at "out-competing" WT cells compared to CD45.2 WT cells.

Example 3

The following experiment was performed to investigate how the absence of IL18 affects hematopoietic reconstitution. Experiments were performed as described above, with the exception that in the previous experiments total bone marrow was used in which is a mixture of cells at different stages of maturation was already present. In these experiments, in order to test whether the absence of IL18 has an effect on de novo generated cells, purified early (i.e. non lineage-committed) progenitors were transplanted which were defined as lineage-negative Kit+Sca1+ cells. This was followed by peripheral blood reconstitution 2-weekly.

Figure 4:
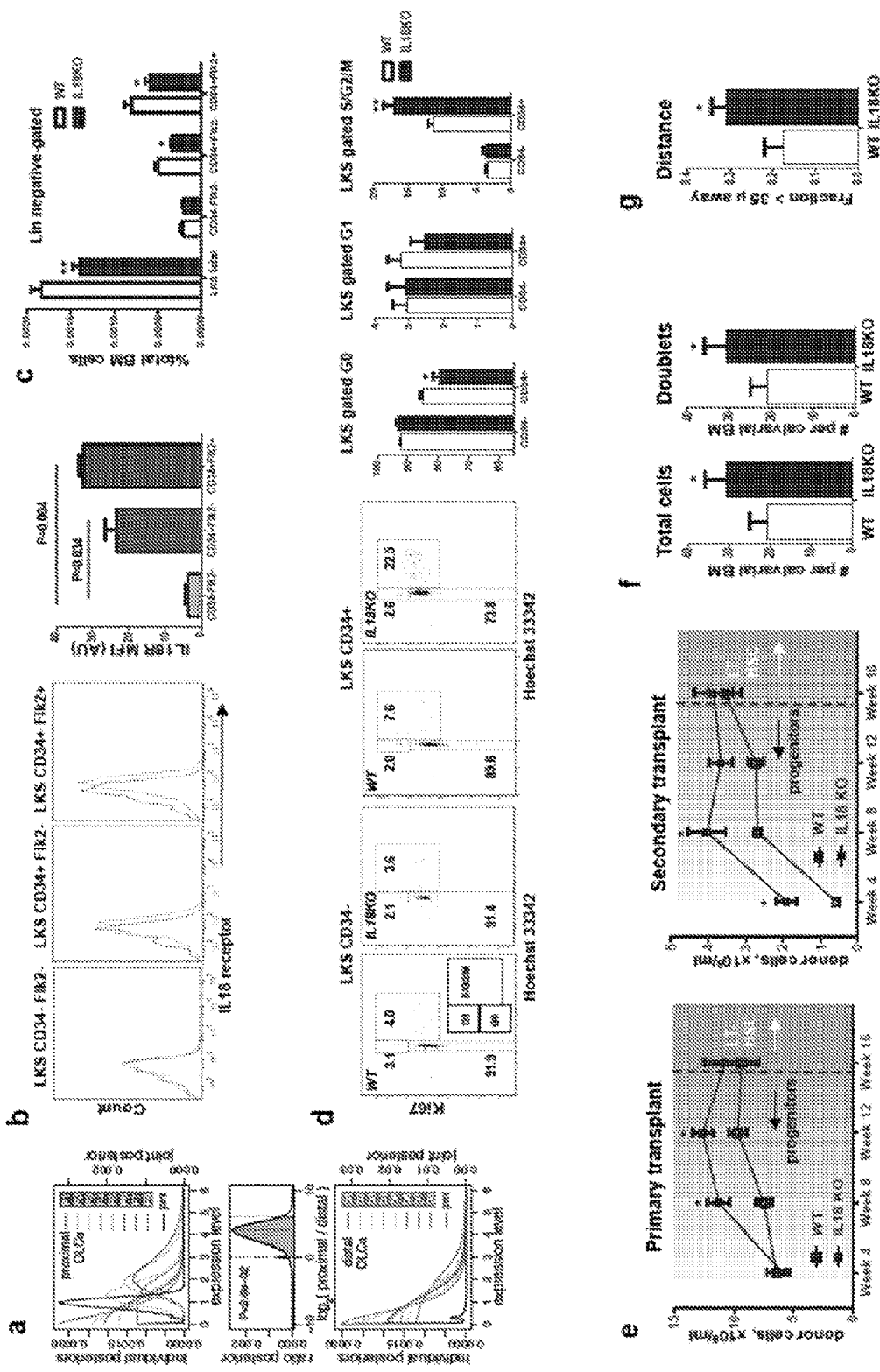
FIG. 4A-FIG. 4E show experimental results that indicate interleukin-18 is a novel non-cell autonomous hematopoietic regulator. A) Single-cell RNA-Seq data demonstrated elevated expression of IL18 in HSPC-proximal OLCs. B) IL18R1 is predominantly expressed in LKS $CD34^+Flk2^-$ and LKS $CD34^+Flk2^+$ hematopoietic progenitors. Shown are representative histograms (left panel) and IL18R1 mean fluorescence intensity (right panel, n=3). Bone marrow mononuclear cells from IL18R1 KO mouse were used as a negative control (red line). C) Reduced frequency of LKS $CD34^+Flk2^-$ and LKS $CD34^+Flk2^+$ hematopoietic progenitors in IL18KO mice (n=12 per group). D) Loss of quiescence in LKS $CD34^+Flk2^-$ and LKS $CD34^+Flk2^+$ hematopoietic progenitors in IL18KO mice, as assessed by Ki67/Hoechst 33342 staining Shown are FACS plots from a representative experiment (right panel, numbers indicate the percentage cells in each phase of the cell cycle) and a cumulative diagram (n=7 per group). E) Transplanted WT bone marrow cells display faster early hematopoietic reconstitution in the IL18KO recipients, as assessed by peripheral blood chimerism analysis in primary (left) and secondary transplants (right, n=4-7 per group). F) and G) Transplanted WT LKS cells proliferate faster and display altered localization in the IL18-deficient microenvironment. At 24 hours, the transplanted cells formed a greater number of doublets in the IL18KO mice and were located further away from the endosteal surface (left panel, n=6 per group). *p<0.05, **p<0.01.
Figure 11:
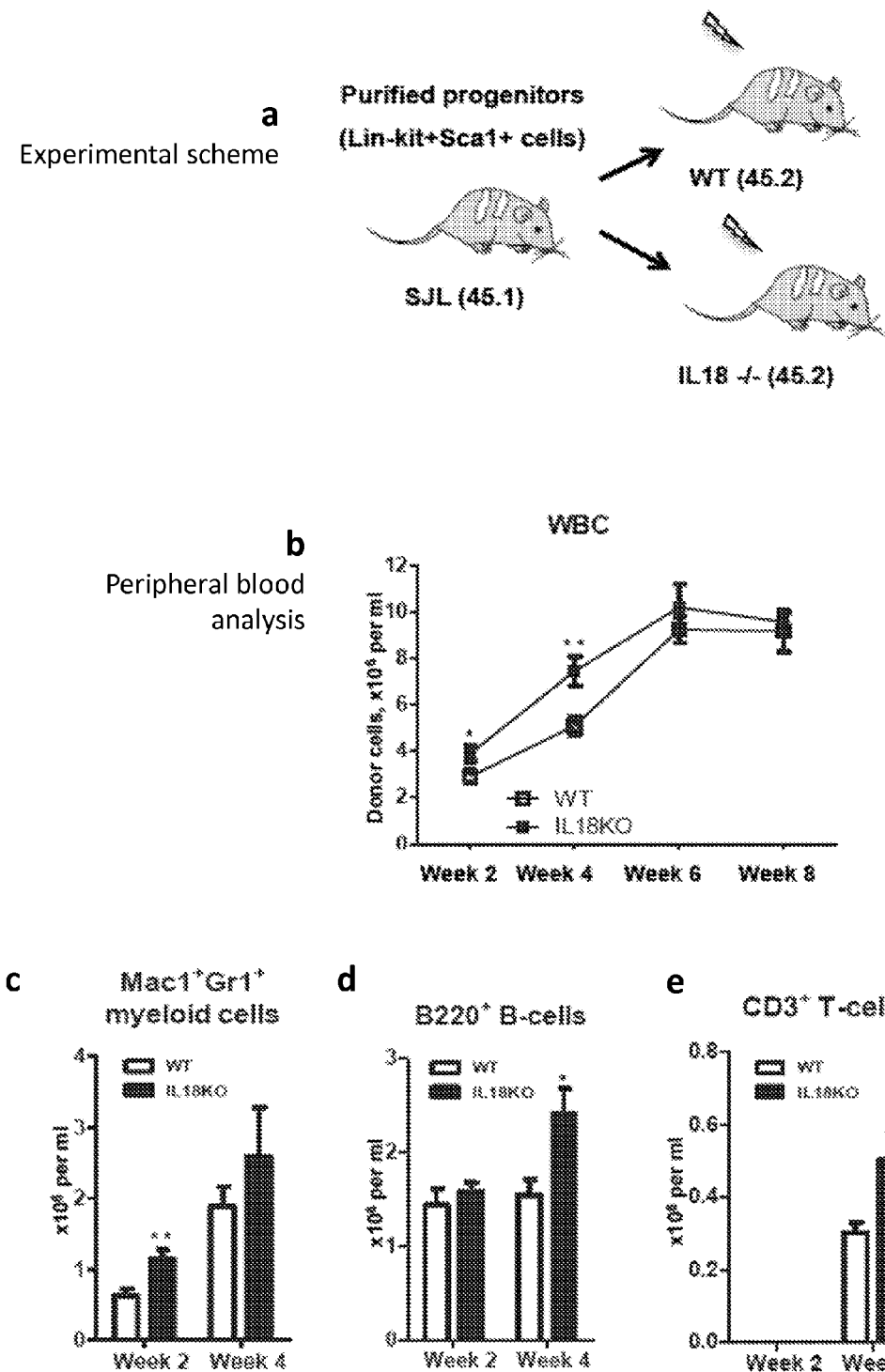
FIG. 11A-FIG. 11E show experimental results that indicate purified hematopoietic progenitors display faster myeloid and lymphoid reconstitution in the absence of IL18. A) shows the experimental schema. B) shows peripheral blood analysis of white blood cells to week 8. C) shows peripheral blood analysis of Mac1+Gr1+ myeloid cells at week 2 and week 4. D) shows peripheral blood analysis of B220+ B-cells at week 2 and week 4. E) shows peripheral blood analysis of CD3+ T-cells at week 2 and week 4.
Figure 15:
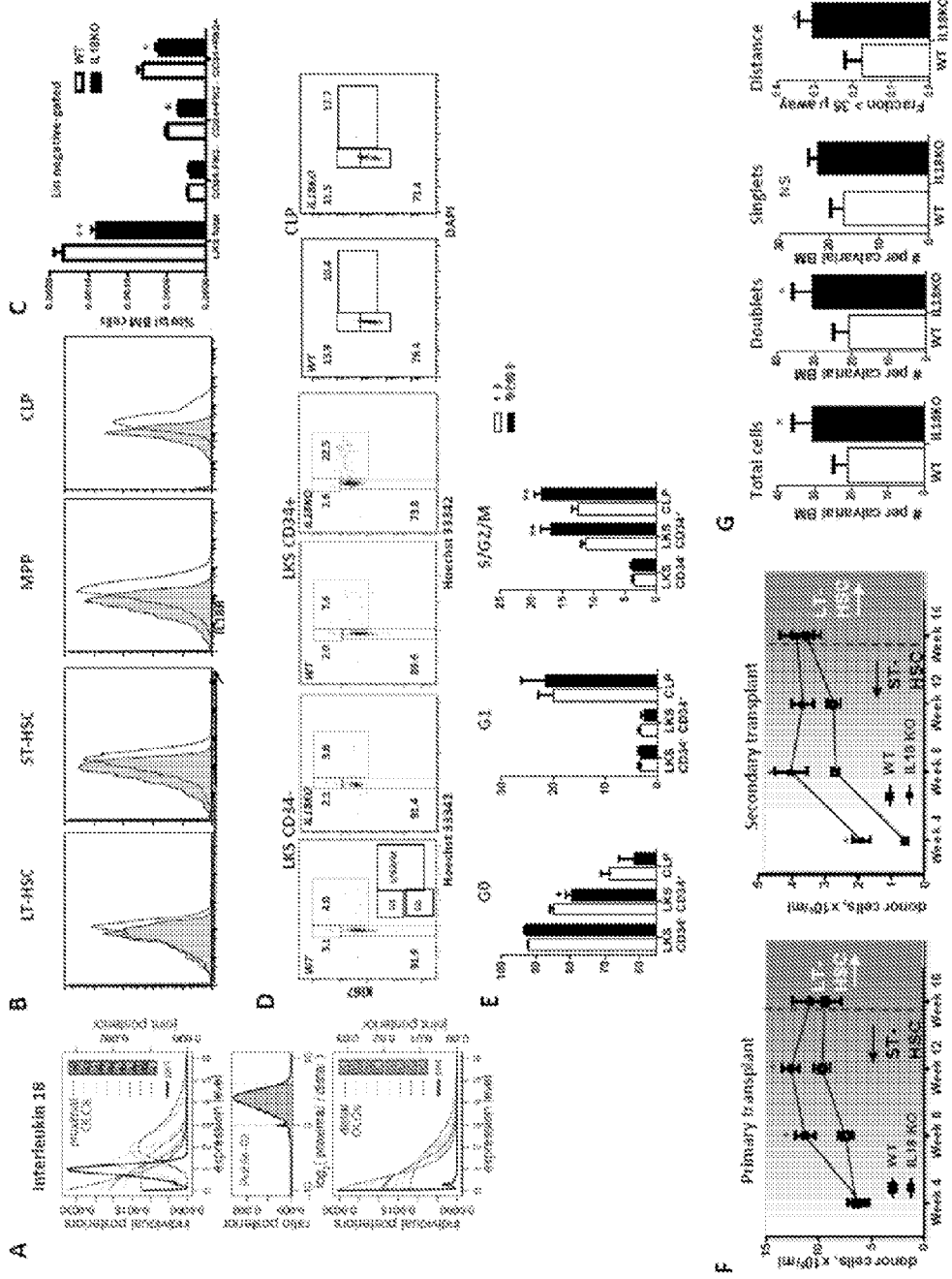
FIG. 15A-FIG. 15G is a collection of experimental results that indicate IL-18 is expressed in the osteolineage (OLCs) cells which are proximal to transplanted HSPC.

Just as with the total bone marrow, the reconstitution was enhanced at early time points (FIG. 11). A transient increase was observed in both myeloid (at 2 weeks) and T- and B-lymphoid reconstitution (4 weeks), suggesting that proliferation of a common progenitor for all three cell types was responsible (this progenitor is called multi-potent—MPP—because it differentiates both in lymphoid and myeloid cells). However, an additional effect of IL18 absence on a progenitor which is specific for the lymphoid cells (common lymphoid progenitor—CLP) on enhanced lymphoid reconstitution appears likely, given that CLP express high level of IL18R and cycle faster in IL18KO mice (FIG. 4 and FIG. 15).

The results of these experiments indicate that the absence of IL18 results in reconstitution post-transplant, which is mediated by the effect on short-term HSC, multipotent progenitors and common lymphoid progenitors. All the above cell types express IL18R and display increased cycling in IL18KO mouse.

Example 4

Figure 12:
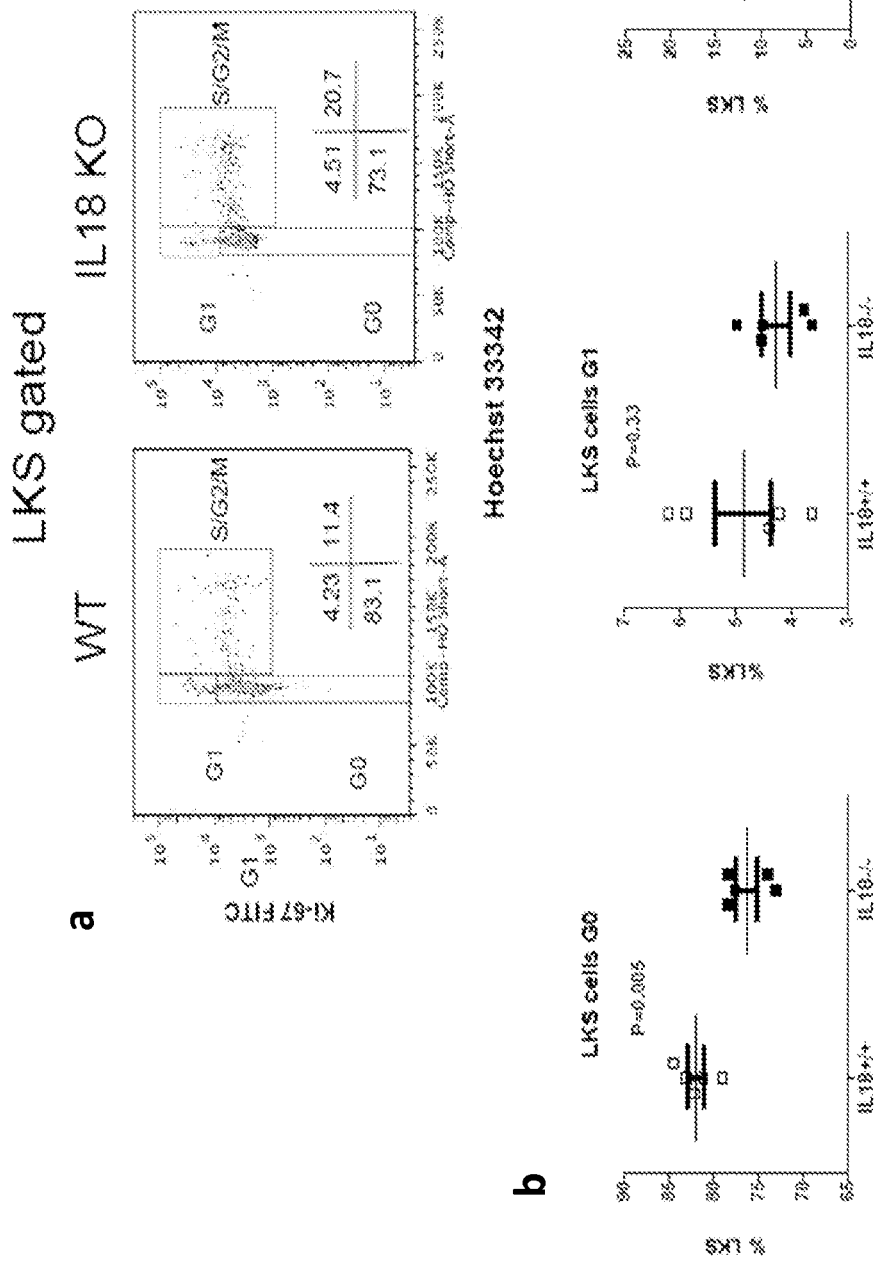
FIG. 12A-FIG. 12B show experimental results that indicate IL18 is a quiescence-inducing factor in HSPC.
Figure 13:
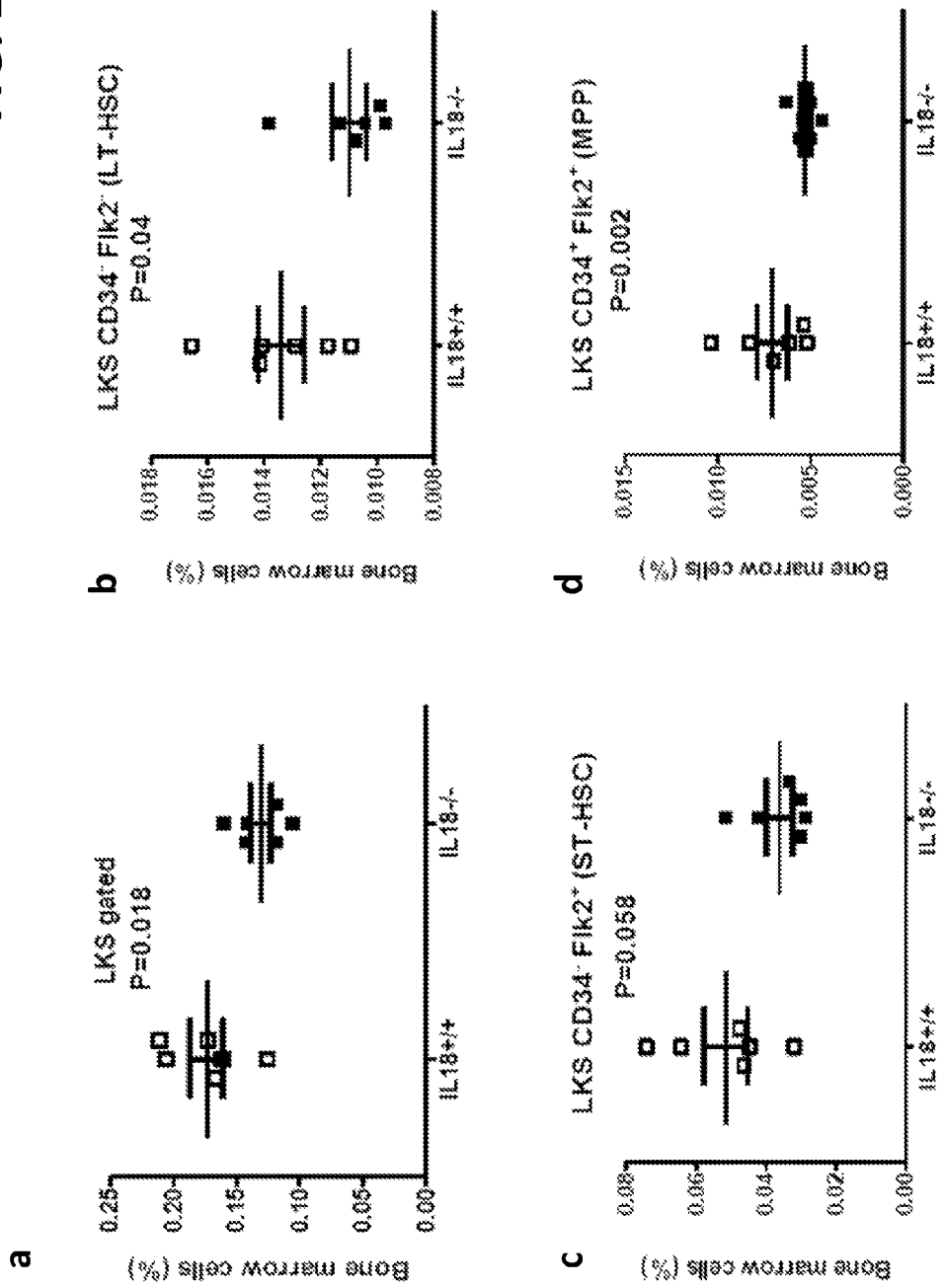
FIG. 13A-FIG. 13D show experimental results that indicate a reduced frequency of primitive hematopoietic cells in IL18−/− mice.
Figure 14:
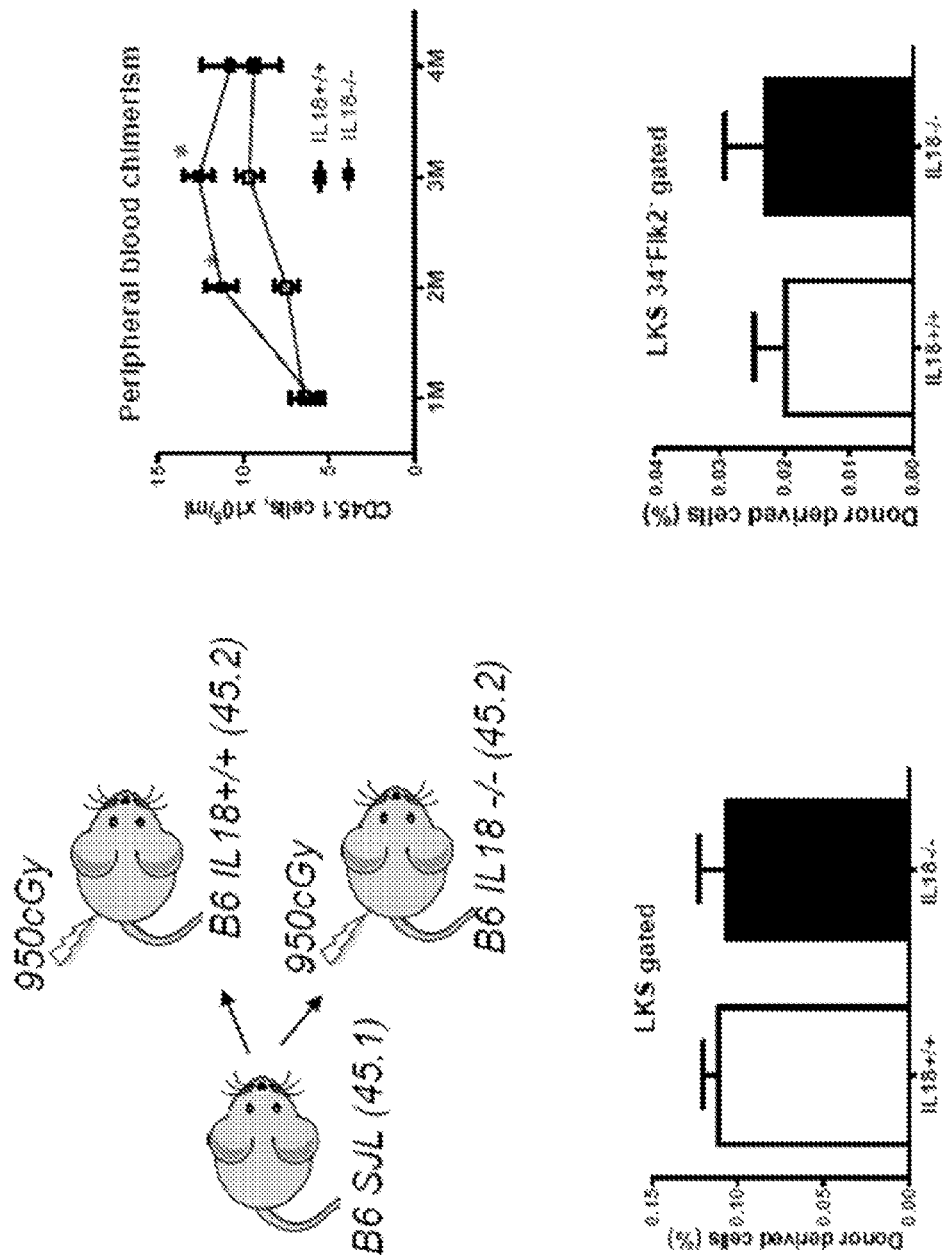
FIG. 14A-FIG. 14D show experimental results that indicate IL18KO mice have enhanced early post-transplant reconstitution. A) Lethally irradiated WT or IL18−/− animals were transplanted with 500K congenic (CD45.1) bone marrow cells. B) Monthly peripheral blood chimerism analysis for CD 45.1 cells revealed a faster hematopoietic reconstitution between 2 months and 3 months post-transplantation in IL18KO animals, indicating faster progenitor expansion. The animals were sacrificed at 16 weeks and the bone marrow examined. No difference in the overall cellularity or stem cell numbers was observed (C, D) at this time point, indicating that the absence of IL-18 affects hematopoiesis in the early post-transplant period, predominantly at the progenitor level.

Strategies to enhance early progenitor expansion in order to reduce the risk of infectious and hemorrhagic complications in the first few weeks post-transplant are likely to reduce post-transplant morbidity and mortality. The results from the experiments described herein (FIGS. 12, 13 and 14)) indicate a method for early hematopoietic progenitor expansion by inhibition of IL18-IL18 receptor signaling using an inhibitor of IL18-IL18 receptor signaling, such as IL18-binding protein. IL18 receptor is expressed at a much higher level in hematopoietic progenitors compared to stem cells, in which IL18R expression is almost undetectable. Consistently, a significant increase in the number of mature cells (neutrophils, and lymphocytes) was observed in the peripheral blood 4-8 week period post-transplant, in the IL18 KO mice, without a numeric change in the number of long-term HSCs at 16 weeks post-transplant. This indicates that short-term (5 days) inhibition of IL18 signaling, in the donor prior to peripheral blood stem cell/bone marrow harvest and/or in the recipient after the transplant, will produce a short-term increase in a proliferative capacity of hematopoietic progenitors and reduce the risk of life-threatening cytopenias in the recipient. Given that the IL18-inhibitor will be used short-term, no adverse effect on immunological function are anticipated. Although there is no available data on half-life of IL18-BP, the half-life of recombinant IL18 itself which was given to human patients is estimated at 35 hours (Robertson et al. Clin Cancer Res. 2006; 12:4265-4273).

Example 5

Interleukin 18 was found to be expressed in the osteolineage (OLCs) cells which are proximal to transplanted HSPC. As shown in FIG. 4A, three out of 8 single osteolineage cells expressed this molecule, whereas none of the distal OLCs did. Studies of interleukin 18 receptor expression on hematopoietic stem and progenitor cells by flow cytometry (FIG. 15B) demonstrated its presence on the cell surface of several subsets of primitive hematopoietic cells such as short-term HSC, multi-potent progenitor (MPP) and common lymphoid progenitor (CLP), but not long-term HSC (LT-HSC). ST-HSC and MPP were also reduced in frequency in IL18KO mice (FIG. 15C) while CLP frequency did not change. Cell cycle studies (FIGS. 15D and 15E) revealed that in the absence of IL18, those cell subsets which express the receptor appear to cycle faster, suggesting that IL18 acts as a non-autonomous regulator of quiescence. Consistently, wild-type bone marrow cells transplanted into myeloablated IL18KO recipients display faster short-term reconstitution (FIG. 15F). In-vivo imaging studies show that even after 24 hours, transplanted LKS cells proliferate faster in the IL18KO environment and home further from the endosteum (FIG. 15G).

REFERENCES

1. Scadden, D. T. The stem-cell niche as an entity of action. *Nature* 441, 1075-9 (2006).
2. Frenette, P. S., Pinho, S., Lucas, D. & Scheiermann, C. Mesenchymal stem cell: keystone of the hematopoietic stem cell niche and a stepping-stone for regenerative medicine. *Annu Rev Immunol* 31, 285-316 (2013).
3. Okamura, H. et al. Cloning of a new cytokine that induces IFN-gamma production by T cells. *Nature* 378, 88-91 (1995).
4. Moore, K. A. & Lemischka, I. R. Stem cells and their niches. *Science* 311, 1880-5 (2006).
5. Xie, T. & Spradling, A. C. A niche maintaining germ line stem cells in the Drosophila ovary. *Science* 290, 328-30 (2000).
6. Calvi, L. M. et al. Osteoblastic cells regulate the haematopoietic stem cell niche. *Nature* 425, 841-6 (2003).
7. Zhang, J. et al. Identification of the haematopoietic stem cell niche and control of the niche size. *Nature* 425, 836-41 (2003).
8. Ding, L. & Morrison, S. J. Haematopoietic stem cells and early lymphoid progenitors occupy distinct bone marrow niches. *Nature* 495, 231-5 (2013).
9. Ding, L., Saunders, T. L., Enikolopov, G. & Morrison, S. J. Endothelial and perivascular cells maintain haematopoietic stem cells. *Nature* 481, 457-62 (2012).

10. Mendez-Ferrer, S. et al. Mesenchymal and haematopoietic stem cells form a unique bone marrow niche. *Nature* 466, 829-34 (2010).
11. Greenbaum, A. et al. CXCL12 in early mesenchymal progenitors is required for haematopoietic stem-cell maintenance. *Nature* 495, 227-30 (2013).
12. Raaijmakers, M. H. et al. Bone progenitor dysfunction induces myelodysplasia and secondary leukaemia. *Nature* 464, 852-7 (2010).
13. Lo Celso, C. et al. Live-animal tracking of individual haematopoietic stem/progenitor cells in their niche. *Nature* 457, 92-6 (2009).
14. Tang, F. et al. mRNA-Seq whole-transcriptome analysis of a single cell. *Nat Methods* 6, 377-82 (2009).
15. Kalajzic, Z. et al. Directing the expression of a green fluorescent protein transgene in differentiated osteoblasts: comparison between rat type I collagen and rat osteocalcin promoters. *Bone* 31, 654-60 (2002).
16. Eldar, A. & Elowitz, M. B. Functional roles for noise in genetic circuits. *Nature* 467, 167-73 (2010).
17. Kharchenko, P. V., Silberstein, L. & Scadden, D. T. Baeysian approach to single-cell differential expression analysis. *In submission*.
18. Arai, F. et al. Tie2/angiopoietin-1 signaling regulates hematopoietic stem cell quiescence in the bone marrow niche. *Cell* 118, 149-61 (2004).
19. Vermeulen, M. et al. Role of adhesion molecules in the homing and mobilization of murine hematopoietic stem and progenitor cells. *Blood* 92, 894-900 (1998).
20. Hattori, K. et al. Placental growth factor reconstitutes hematopoiesis by recruiting VEGFR1(+) stem cells from bone-marrow microenvironment. *Nat Med* 8, 841-9 (2002).
21. Heissig, B. et al. Recruitment of stem and progenitor cells from the bone marrow niche requires MMP-9 mediated release of kit-ligand. *Cell* 109, 625-37 (2002).
22. Sugimura, R. et al. Noncanonical Wnt signaling maintains hematopoietic stem cells in the niche. *Cell* 150, 351-65 (2012).
23. Nagasawa, T. et al. Defects of B-cell lymphopoiesis and bone-marrow myelopoiesis in mice lacking the CXC chemokine PBSF/SDF-1. *Nature* 382, 635-8 (1996).
24. Huang, R. P., Ozawa, M., Kadomatsu, K. & Muramatsu, T. Embigin, a member of the immunoglobulin superfamily expressed in embryonic cells, enhances cell-substratum adhesion. *Dev Biol* 155, 307-14 (1993).
25. Amin, M. A. et al. Interleukin-18 induces angiogenic factors in rheumatoid arthritis synovial tissue fibroblasts via distinct signaling pathways. *Arthritis Rheum* 56, 1787-97 (2007).
26. Vidal-Vanaclocha, F. et al. IL-18 regulates IL-1beta-dependent hepatic melanoma metastasis via vascular cell adhesion molecule-1. *Proc Natl Acad Sci USA* 97, 734-9 (2000).
27. Takeda, K. et al. Defective NK cell activity and Th1 response in IL-18-deficient mice. *Immunity* 8, 383-90 (1998).
28. Muzumdar, M. D., Tasic, B., Miyamichi, K., Li, L. & Luo, L. A global double-fluorescent Cre reporter mouse. *Genesis* 45, 593-605 (2007).
29. Kollet, O. et al. Osteoclasts degrade endosteal components and promote mobilization of hematopoietic progenitor cells. *Nat Med* 12, 657-64 (2006).
30. Chow, A. et al. Bone marrow CD169+ macrophages promote the retention of hematopoietic stem and progenitor cells in the mesenchymal stem cell niche. *J Exp Med* 208, 261-71 (2011).
31. Udagawa, N. et al. Interleukin-18 (interferon-gamma-inducing factor) is produced by osteoblasts and acts via granulocyte/macrophage colony-stimulating factor and not via interferon-gamma to inhibit osteoclast formation. *J Exp Med* 185, 1005-12 (1997).
32. Gerdes, N. et al. Expression of interleukin (IL)-18 and functional IL-18 receptor on human vascular endothelial cells, smooth muscle cells, and macrophages: implications for atherogenesis. *J Exp Med* 195, 245-57 (2002).
33. Christensen, J. L. & Weissman, I. L. Flk-2 is a marker in hematopoietic stem cell differentiation: a simple method to isolate long-term stem cells. *Proc Natl Acad Sci USA* 98, 14541-6 (2001).
34. Karsunky, H., Inlay, M. A., Serwold, T., Bhattacharya, D. & Weissman, I. L. Flk2+ common lymphoid progenitors possess equivalent differentiation potential for the B and T lineages. *Blood* 111, 5562-70 (2008).
35. Bruscia, E. M. et al. Engraftment of donor-derived epithelial cells in multiple organs following bone marrow transplantation into newborn mice. *Stem Cells* 24, 2299-308 (2006).
36. Sands, M. S. & Barker, J. E. Percutaneous intravenous injection in neonatal mice. *Lab Anim Sci* 49, 328-30 (1999).

What is claimed:

1. A method for enhancing hematopoietic reconstitution of a subject in need thereof comprising:
   a) administering to the subject hematopoietic stem/progenitor cells (HSPC) obtained from the blood, placenta or umbilical cord of a donor; and
   b) administering to the subject a therapeutically effective amount of an inhibitor of interleukin 18 (IL-18) to thereby inhibit IL-18 interaction with IL-18R molecules present on the HSPC administered in step a).

2. The method of claim 1, wherein administering step b) is by a route selected from the group consisting of enteral and parenteral.

3. The method of claim 2, wherein administering step b) is performed immediately after administering step a).

4. The method of claim 2, wherein administering step b) is performed prior to and immediately after administering step a).

5. The method of claim 1, wherein the inhibitor of IL-18 is administered to the subject over a period of time from about 1 day to 100 days directly after administration of the HSPCs.

6. The method of claim 5, wherein the period is from about 1 day to about 21 days directly after administration of the HSPCs.

7. The method of claim 5, wherein the period is from about 1 day to about 5 days directly after administration of the HSPCs.

8. The method of claim 5, wherein the period is about 5 days directly after administration of the HSPCs.

9. The method of claim 1, wherein the HSPCs are allogenic.

10. The method of claim 1, wherein the HSPCs are autologous.

11. The method of claim 1 wherein the HSPC are obtained from a donor subject treated with an inhibitor of IL-18 prior to harvest of the HSPCs to thereby expand early hematopoietic progenitor cells in the HSPCs.

12. The method of claim 11, wherein the treatment of the donor subject is by administration of the inhibitor of IL-18 to the donor subject by a method selected from the group consisting of enteral and parenteral.

13. The method of claim 1, wherein the inhibitor of IL-18 is selected from the group consisting of IL-18 binding protein, an antibody against IL-18, an antibody against an IL-18 receptor subunits, an inhibitor of the IL-18 signaling pathway, an antagonist of IL-18 which competes with IL-18 and blocks the IL-18 receptor, an inhibitor of caspase-1 (ICE), an IL-18 isoform, an IL-18 mutein, an IL-18 fused protein, an IL-18 functional derivative, an IL-18 active fraction, and an IL-18 circularly permutated derivative thereof inhibiting the biological activity of IL-18.

14. A method for enhanced hematopoietic reconstitution in a subject in need thereof comprising administering to the subject hematopoietic stem/progenitor cells (HSPC) obtained from a donor subject, wherein the donor subject was treated with an inhibitor of interleukin 18 (IL-18) to thereby expand early hematopoietic progenitor cells prior to harvest of the HSPCs from the donor.

15. The method of claim 14, wherein the donor subject is treated with the inhibitor of IL-18 for a period of from about 1 day to about 10 days directly prior to harvest of the HSPCs.

16. The method of claim 15, wherein the period is from about 1 day to about 5 days directly prior to harvest of the HSPCs.

17. The method of claim 15, wherein the period is about 5 days directly prior to harvest of the HSPCs.

18. The method of claim 14, wherein the HSPCs are obtained from bone marrow, blood, placenta, or umbilical cord of the donor.

19. The method of claim 14, wherein the inhibitor of IL-18 is selected from the group consisting of IL-18 binding protein, an antibody against IL-18, an antibody against an IL-18 receptor subunits, an inhibitor of the IL-18 signaling pathway, an antagonist of IL-18 which competes with IL-18 and blocks the IL-18 receptor, an inhibitor of caspase-1 (ICE), an IL-18 isoform, an IL-18 mutein, an IL-18 fused protein, an IL-18 functional derivative, an IL-18 active fraction, and an IL-18 circularly permutated derivative thereof inhibiting the biological activity of IL-18.

20. A method for enhancing hematopoietic reconstitution of a subject in need thereof comprising:
   a) administering to the subject autologous hematopoietic stem/progenitor cells (HSPC); and
   b) administering to the subject a therapeutically effective amount of an inhibitor of interleukin 18 (IL-18) to thereby inhibit IL-18 interaction with IL-18R molecules present on the HSPC administered in step a).

* * * * *

SEQUENCE LISTING

```
<160> NUMBER OF SEQ ID NOS: 11

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atgaatacgg ctacagg                                                      17

<210> SEQ ID NO 2
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 2
ctcttgctga gtgtccttgc tg                                                  22

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caacactcca aactgtgccc ttca                                                24

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tccttgggct gttgtgctta ct                                                  22

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccttgtacca cgaggatagg                                                     20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cccacccttc cctcactcat                                                     20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtatctgcca caatggcacg                                                     20

<210> SEQ ID NO 8
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 8
cttcattgca ttgcacgtca t                                               21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccatctttct gctcactctg c                                               21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tggacatgaa ggctttgtca                                                 20

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Phe Gly Ala Gly Leu Val Leu Gly Gly Gln Phe Met
1               5                   10
```